(12) United States Patent
Simanzhenkov et al.

(10) Patent No.: US 11,447,434 B2
(45) Date of Patent: Sep. 20, 2022

(54) MITIGATING OXYGEN, CARBON DIOXIDE AND/OR ACETYLENE OUTPUT FROM AN ODH PROCESS

(71) Applicant: NOVA Chemicals (International) S.A., Fribourg (CH)

(72) Inventors: Vasily Simanzhenkov, Calgary (CA); Shahin Goodarznia, Calgary (CA); Kamal Serhal, Calgary (CA); Xiaoliang Gao, Calgary (CA); Yoonhee Kim, Calgary (CA)

(73) Assignee: NOVA Chemicals (International) S.A., Fribourg (CH)

( * ) Notice: Subject to any disclaimer, the term of this patent is extended or adjusted under 35 U.S.C. 154(b) by 0 days.

(21) Appl. No.: 16/977,587

(22) PCT Filed: Mar. 8, 2019

(86) PCT No.: PCT/IB2019/051918
§ 371 (c)(1),
(2) Date: Sep. 2, 2020

(87) PCT Pub. No.: WO2019/175731
PCT Pub. Date: Sep. 19, 2019

(65) Prior Publication Data
US 2020/0407289 A1    Dec. 31, 2020

Related U.S. Application Data

(60) Provisional application No. 62/741,705, filed on Oct. 5, 2018, provisional application No. 62/642,265, filed on Mar. 13, 2018.

(51) Int. Cl.
*C07C 5/48* (2006.01)
*C01B 32/50* (2017.01)
(Continued)

(52) U.S. Cl.
CPC .............. *C07C 5/48* (2013.01); *B01J 23/50* (2013.01); *C01B 32/40* (2017.08); *C01B 32/50* (2017.08); *C07C 11/04* (2013.01)

(58) Field of Classification Search
CPC . C07C 5/84; C01B 32/50; C01B 32/40; B01J 23/50
See application file for complete search history.

(56) References Cited

U.S. PATENT DOCUMENTS 3,444,264 A * 5/1969 Fernald ............... C07C 11/02
585/503
5,500,198 A * 3/1996 Liu .................... B01D 53/864
423/245.3
(Continued)

FOREIGN PATENT DOCUMENTS

EP         2871251 A1   5/2015
WO   WO-0224614 A1 *  3/2002  ............ C07C 2/84
(Continued)

OTHER PUBLICATIONS

Mamontov, G.V.; Gorbunova, A.S.; Vyshegorodsteva, E.V.; Zaikovskii, V.I.; Vodyankina, O.V.; Selective oxidation of CO in the presence of propylene over Ag/MCM-41 catalyst; Catalysis Today (2019); 333—pp. 245-250.

(Continued)

*Primary Examiner* — Youngsul Jeong
(74) *Attorney, Agent, or Firm* — Fish & Richardson P.C.

(57) ABSTRACT

A method of converting one or more alkanes to one or more alkenes that includes a) providing a first stream containing one or more alkanes and oxygen to an oxidative dehydrogenation reactor; b) converting at least a portion of the one or more alkanes to one or more alkenes in the oxidative dehydrogenation reactor to provide a second stream exiting the oxidative dehydrogenation reactor containing one or more alkanes, one or more alkenes, oxygen, carbon mon- (Continued)

oxide and optionally acetylene; and c) providing the second stream to a second reactor containing a catalyst that includes a group 11 metal to convert a least a portion of the carbon monoxide to carbon dioxide and reacting the acetylene.

19 Claims, 7 Drawing Sheets

(51) Int. Cl.
*C01B 32/40* (2017.01)
*B01J 23/50* (2006.01)
*C07C 11/04* (2006.01)

(56) References Cited

U.S. PATENT DOCUMENTS

| | | | |
|---|---|---|---|
| 6,436,202 B1 | 8/2002 | Benum et al. | |
| 6,518,476 B1* | 2/2003 | Culp | C07C 11/02 585/655 |
| 6,723,298 B1* | 4/2004 | Baumann | B01J 37/0205 423/655 |
| 6,824,883 B1 | 11/2004 | Benum et al. | |
| 6,899,966 B2 | 5/2005 | Benum et al. | |
| 7,156,979 B2 | 1/2007 | Benum et al. | |
| 7,488,392 B2 | 2/2009 | Benum et al. | |
| 7,838,710 B2* | 11/2010 | Ryu | B01J 23/8946 585/274 |
| 8,519,210 B2* | 8/2013 | Arnold | C07C 5/48 585/663 |
| 8,568,538 B2 | 10/2013 | Kerber | |
| 8,642,825 B2 | 2/2014 | Kustov et al. | |
| 8,846,996 B2 | 9/2014 | Kustov et al. | |
| 9,073,036 B2* | 7/2015 | Hagemeyer | C07C 51/16 |
| 9,197,613 B2 | 11/2015 | Chiueh et al. | |
| 9,545,610 B2 | 1/2017 | Simanzhenkov et al. | |
| 9,550,709 B2 | 1/2017 | Simanzhenkov et al. | |
| 9,963,412 B2 | 5/2018 | Bos et al. | |
| 9,993,798 B2 | 6/2018 | Simanzhenkov et al. | |
| 10,017,432 B2 | 7/2018 | Bos et al. | |
| 10,343,957 B2 | 7/2019 | Serhal et al. | |
| 2006/0142508 A1† | 6/2006 | Shamshoum | |
| 2016/0326070 A1* | 11/2016 | Winkler | C07C 5/48 |
| 2017/0050178 A1 | 2/2017 | Simanzhenkov et al. | |
| 2020/0002251 A1† | 1/2020 | Mitkidis | |

FOREIGN PATENT DOCUMENTS

| | | | |
|---|---|---|---|
| WO | 2010115108 | † | 10/2010 |
| WO | WO 2014010680 | | 1/2014 |
| WO | 2017/046315 A1 | | 3/2017 |
| WO | 2017/072086 A1 | | 5/2017 |
| WO | WO-2017072086 A1 * | 5/2017 | ........... C07C 51/215 |
| WO | 2017/144584 A1 | | 8/2017 |
| WO | 2018/019760 A1 | | 2/2018 |
| WO | 2018/024650 A1 | | 2/2018 |

OTHER PUBLICATIONS

Mamontov, G.V.; Grabchenko, M.V.; Litvyakova, N.N.; Gorbunova, A.S.; Dutov, V.V.; Zaikovskii, V.I.; Vodyankina, O.V.; Selective oxidation of CO in the presence of propylene over AG/SiO2 catalysts; 8th World Congress on Oxidation Catalysis & XII European Workshop Meeting in Innovation in Selective Oxidation Catalysis (ISO'17), Sep. 3-8, 2017, Krakow, Poland—Book of Abstracts, p. 111.

Dury et al., "The active role of CO2 at low temperature in oxidation processes: the case of the oxidative dehydrogenation of propane on NiMoO4 catalysts," Applied Catalysis A: General, Mar. 2003, 242(1):187-203.

International Search Report and Written Opinion in International Appln. No. PCT/IB2019/051918, dated Dec. 6, 2019, 11 pages.

[No Author Listed], "Chemical process," Research Disclosure Database No. 338030, Jun. 1992, 8 pages.

\* cited by examiner
† cited by third party ized polymers. Since naturally occurring sources of olefins do not exist in commercial quantities polymer producers rely on methods for converting the more abundant lower alkanes into olefins. The method of choice for today's commercial scale producers is steam cracking, a highly endothermic process where steam-diluted alkanes are subjected very briefly to a temperature of at least 800° C. The fuel demand to produce the required temperatures and the need for equipment that can withstand that temperature add significantly to the overall cost. Also, the high temperature promotes the formation of coke which accumulates within the system, resulting in the need for costly periodic reactor shut-down for maintenance and coke removal.

MITIGATING OXYGEN, CARBON DIOXIDE AND/OR ACETYLENE OUTPUT FROM AN ODH PROCESS

The present disclosure relates generally to oxidative dehydrogenation (ODH) of lower alkanes into corresponding alkenes. In some embodiments, the present disclosure relates to controlling the carbon dioxide output levels from an ODH process.

Olefins like ethylene, propylene, and butylene, are basic building blocks for a variety of commercially valuable polymers. Since naturally occurring sources of olefins do not exist in commercial quantities polymer producers rely on methods for converting the more abundant lower alkanes into olefins. The method of choice for today's commercial scale producers is steam cracking, a highly endothermic process where steam-diluted alkanes are subjected very briefly to a temperature of at least 800° C. The fuel demand to produce the required temperatures and the need for equipment that can withstand that temperature add significantly to the overall cost. Also, the high temperature promotes the formation of coke which accumulates within the system, resulting in the need for costly periodic reactor shut-down for maintenance and coke removal.

Oxidative dehydrogenation (ODH) is an alternative to steam cracking that is exothermic and produces little or no coke. In ODH a lower alkane, such as ethane, is mixed with oxygen in the presence of a catalyst and optionally an inert diluent, such as carbon dioxide or nitrogen, in some embodiments at temperatures as low as 300° C., to produce the corresponding alkene. In some embodiments, various other oxidation products, most notably carbon dioxide and acetic acid may also be produced in this process. In some embodiments ODH suffers from lower conversion rates when compared to steam cracking, a fact that when combined with lower selectivity and the risk of thermal explosion due to mixing of a hydrocarbon with oxygen, may have prevented ODH from achieving widespread commercial implementation.

Figure 1:
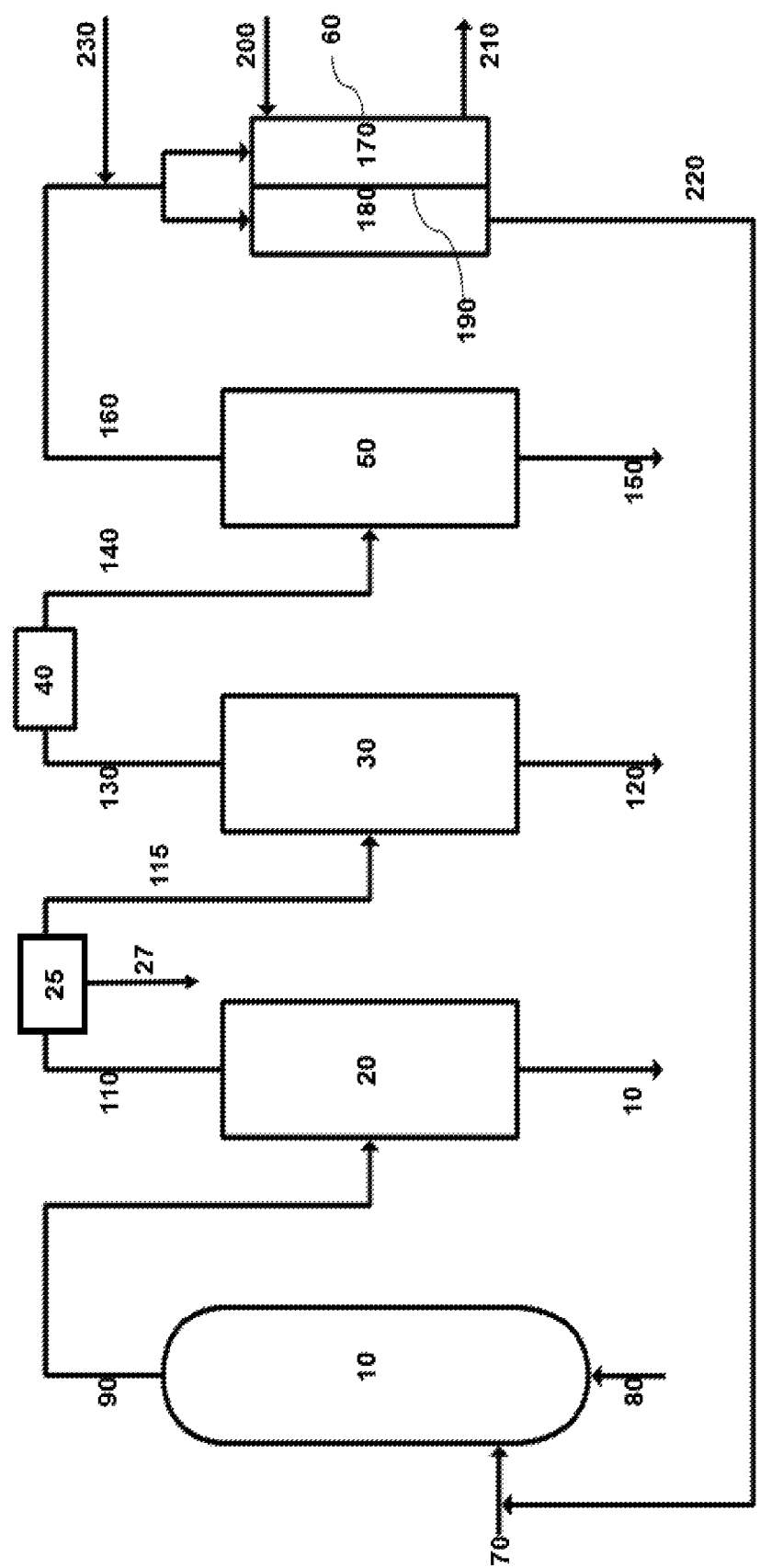
FIG. 1 is a graphic depiction of a chemical complex according to some embodiments of the disclosure.

Other than in the operating examples or where otherwise indicated, all numbers or expressions referring to quantities of ingredients, reaction conditions, etc. used in the specification and claims are to be understood as modified in all instances by the term "about". Accordingly, unless indicated to the contrary, the numerical parameters set forth in the following specification and attached claims are approximations that can vary depending upon the desired properties, which the present disclosure desires to obtain. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical values, however, inherently contain certain errors necessarily resulting from the standard deviation found in their respective testing measurements.

Also, it should be understood that any numerical range recited herein is intended to include all sub-ranges subsumed therein. For example, a range of "1 to 10" is intended to include all sub-ranges between and including the recited minimum value of 1 and the recited maximum value of 10; that is, having a minimum value equal to or greater than 1 and a maximum value of equal to or less than 10. Because the disclosed numerical ranges are continuous, they include every value between the minimum and maximum values. Unless expressly indicated otherwise, the various numerical ranges specified in this application are approximations.

As used herein, the term "alkane" refers to an acyclic saturated hydrocarbon. In many cases, an alkane consists of hydrogen and carbon atoms arranged in a linear structure in which all of the carbon-carbon bonds are single bonds. Alkanes have the general chemical formula $C_nH_{2n+2}$. In many embodiments of the disclosure, alkane refers to one or more of ethane, propane, butane, pentane, hexane, octane, decane and dodecane. In particular embodiments, alkane refers to ethane and propane and, in some embodiments, ethane.

As used herein, the term "alkene" refers to unsaturated hydrocarbons that contain at least one carbon-carbon double bond. In many embodiments, alkene refers to alpha olefins. In many embodiments of the disclosure, alkene refers to one or more of ethylene, propylene, 1-butene, butadiene, pentene, pentadiene, hexene, octene, decene and dodecene. In particular embodiments, alkene refers to ethylene and propylene and, in some embodiments, ethylene.

As used herein, the terms "alpha olefin" or "α-olefin" refer to a family of organic compounds which are alkenes (also known as olefins) with a chemical formula $C_xH_{2x}$, distinguished by having a double bond at the primary or alpha (α) position, In many embodiments of the disclosure, alpha olefin refers to one or more of ethylene, propylene, 1-butene, 1-pentene, 1-hexene, 1-octene, 1-decene and 1-dodecene. In particular embodiments, alpha olefins refer to ethylene and propylene and, in some embodiments, ethylene.

As used herein, the term "essentially free of oxygen" means the amount of oxygen present, if any, remaining in a process stream after the one or more ODH reactors, and in many embodiments after the second reactor as described herein, is low enough that it will not present a flammability or explosive risk to the downstream process streams or equipment.

As used herein, the term "fixed bed reactor" refers to one or more reactors, in series or parallel, often including a cylindrical tube filled with catalyst pellets with reactants flowing through the bed and being converted into products. The catalyst in the reactor may have multiple configurations including, but not limited to, one large bed, several horizontal beds, several parallel packed tubes, and multiple beds in their own shells.

As used herein, the term "fluidized bed reactor" refers to one or more reactors, in series or parallel, often including a fluid (gas or liquid) which is passed through a solid granular catalyst, which can be shaped as tiny spheres, at high enough velocities to suspend the solid and cause it to behave as though it were a fluid.

As used herein, the term "gas phase polyethylene process" refers to a process where a mixture of ethylene, optional alpha olefin comonomers and hydrogen is passed over a catalyst in a fixed or fluidized bed reactor. The ethylene and optional alpha olefins polymerize to form grains of polyethylene, suspended in the flowing gas, which can pass out of the reactor. In some embodiments, two or more of the individual reactors are placed in parallel or in series, each of which are under slightly different conditions, so that the properties of different polyethylenes from the reactors are present in the resulting polyethylene blend. In many cases the catalyst system includes, but is not limited to, chromium catalysts, Ziegler-Natta catalysts, zirconocene catalysts, and metallocene catalysts and combinations thereof.

As used herein, the term "HDPE" refers to high density polyethylene, which generally has a density of greater or equal to 0.941 g/cm$^3$. HDPE has a low degree of branching. HDPE is often produced using chromium/silica catalysts, Ziegler-Natta catalysts or metallocene catalysts.

As used herein, the term "high pressure polyethylene process" refers to converting ethylene gas into a white solid by heating it at very high pressures in the presence of minute quantities of oxygen (about <10 ppm oxygen) at about 1000-3000 bar and at about 80-300° C. In many cases, the high pressure polyethylene process produces LDPE.

As used herein, the term "LDPE" refers to low density polyethylene, which is a polyethylene with a high degree of branching with long chains. Often, the density of a LDPE will range from 0.910-0.940 g/cm$^3$. LDPE is created by free radical polymerization.

As used herein, the term "LLDPE" refers to linear low density polyethylene, which is a polyethylene that can have significant numbers of short branches resulting from copolymerization of ethylene with at least one α-olefin comonomer. In some cases, LLDPE has a density in the range of 0.915-0.925 g/cm$^3$. In many cases, the LLDPE is an ethylene hexene copolymer, ethylene octene copolymer or ethylene butene copolymer. The amount of comonomer incorporated can be from 0.5 to 12 mole %, in some cases from 1.5 to 10 mole %, and in other cases from 2 to 8 mole % relative to ethylene.

As used herein, the term "long-chain branching" refers to a situation where during α-olefin polymerization, a vinyl terminated polymer chain is incorporated into a growing polymer chain. Long branches often have a length that is longer than the average critical entanglement distance of a linear (no long chain branching) polymer chain. In many cases long chain branching affects melt rheological behavior.

As used herein, the term "low pressure polyethylene process" refers to polymerizing ethylene using a catalyst that in many cases includes aluminum at generally lower pressures than the high pressure polyethylene process. In many cases the low pressure polyethylene process is carried out at about 10 to 80 bar and at about 70 to 300° C. In many cases the low pressure polyethylene process provides HDPE. In particular cases, an α-olefin comonomer is included in the low pressure polyethylene process to provide LLDPE.

As used herein, the term "MDPE" refers to medium density polyethylene, which is a polyethylene with some short and/or long chain branching and a density in the range of 0.926 to 0.940 g/cm$^3$. MDPE can be produced using chromium/silica catalysts, Ziegler-Natta catalysts or metallocene catalysts.

As used herein, the term "monomer" refers to small molecules containing at least one double bond that reacts in the presence of a free radical polymerization initiator to become chemically bonded to other monomers to form a polymer.

As used herein, the term "moving bed reactor" refers to reactors in which the catalytic material flows along with the reactants and is then separated from the exit stream and recycled.

As used herein, the term "MoVOx catalyst" refers to a mixed metal oxide having the empirical formula $Mo_{6.5-7.0}V_3O_d$, where d is a number to satisfy the valence of the oxide; a mixed metal oxide having the empirical formula $Mo_{6.25-7.25}V_3O_d$, where d is a number to satisfy the valence of the oxide, or combinations thereof.

As used herein, the term, "olefinic monomer" includes, without limitation, α-olefins, and in particular embodiments ethylene, propylene, 1-butene, 1-hexene, 1-octene and combinations thereof.

As used herein, the term, "oxidative dehydrogenation" or "ODH" refers to processes that couple the endothermic dehydration of an alkane with the strongly exothermic oxidation of hydrogen as is further described herein.

As used herein, the term "polyolefin" refers to a material, which is prepared by polymerizing a monomer composition containing at least one olefinic monomer.

As used herein, the term "polyethylene" includes, without limitation, homopolymers of ethylene and copolymers of ethylene and one or more α-olefins.

As used herein, the term "polypropylene" includes, without limitation, homopolymers of propylene, including isotactic polypropylene and syndiotactic polypropylene and copolymers of propylene and one or more α-olefins.

As used herein, the term "polymer" refers to macromolecules composed of repeating structural units connected by covalent chemical bonds and is meant to encompass, without limitation, homopolymers, random copolymers, block copolymers and graft copolymers.

As used herein, the term "short chain branching" refers to copolymers of ethylene with an α-olefin or with branches of less than about 40 carbon atoms. In many cases, the α-olefin or branches are present at less than 20 wt. %, in some cases less than 15 wt. % of the polyethylene. In many cases, the presence of short chain branches interferes with the formation of the polyethylene crystal structure and is observed as a lower density compared with a linear (no short chain branching) polyethylene of the same molecular weight.

As used herein, the term "solution polyethylene process" refers to processes that polymerize ethylene and one or more optional α-olefins in a mixture of lower alkane hydrocarbons in the presence of one or more catalysts. In some embodiments, two or more of the individual reactors are placed in parallel or in series, each of which can be under slightly different conditions, so that the properties of different polyethylenes from the reactors are present in the resulting polyethylene blend. In many cases the catalysts include, but are not limited to, chromium catalysts, Ziegler-Natta catalysts, zirconocene catalysts, hafnocene catalysts, phosphinimine catalysts and metallocene catalysts and combinations thereof.

As used herein, the term "slurry polyethylene process" refers to single-tube loop reactors, double-tube loop reactors or autoclaves (stirred-tank reactors) used to polymerize ethylene and optional α-olefins in the presence of a catalyst system and a diluent. Non-limiting examples of diluents include isobutane, n-hexane or n-heptane. In some embodiments, two or more of the individual reactors are placed in parallel or in series, each of which can be under slightly different conditions, so that the properties of different polyethylenes from the reactors are present in the resulting polyethylene blend. In many cases the catalyst system includes, but is not limited to, chromium catalysts, Ziegler-Natta catalysts, zirconocene catalysts, hafnocene catalysts, phosphinimine catalysts and metallocene catalysts and combinations thereof.

As used herein, the term "substantially free of acetylene" means the amount of acetylene present, if any, remaining in a process stream after the one or more ODH reactors, and in many embodiments after the second reactor as described herein, is undetectable using the analytical techniques described herein or zero vppm.

As used herein, the term "swing bed type reactor arrangement" is a gas phase reactor system where a first vessel effectively operates as a reactor and a second vessel effectively operates as a regenerator for regenerating the catalyst system. This arrangement can be used with fixed bed as well as fluidized bed gas phase polyethylene reactors.

As used herein, the term "thermoplastic" refers to a class of polymers that soften or become liquid when heated and harden when cooled. In many cases, thermoplastics are high-molecular-weight polymers that can be repeatedly heated and remolded. In many embodiments of the disclosure, thermoplastic resins include polyolefins and elastomers that have thermoplastic properties.

As used herein, the terms "thermoplastic elastomers" and "TPE" refer to a class of copolymers or a blend of polymers (in many cases a blend of a thermoplastic and a rubber) which includes materials having both thermoplastic and elastomeric properties.

As used herein, the terms "thermoplastic olefin" or "TPO" refer to polymer/filler blends that contain some fraction of polyethylene, polypropylene, block copolymers of polypropylene, rubber, and a reinforcing filler. The fillers can include, without limitation, talc, fiberglass, carbon fiber, wollastonite, and/or metal oxy sulfate. The rubber can include, without limitation, ethylene-propylene rubber, EPDM (ethylene-propylene-diene rubber), ethylene-butadiene copolymer, styrene-ethylene-butadiene-styrene block copolymers, styrene-butadiene copolymers, ethylene-vinyl acetate copolymers, ethylene-alkyl (meth)acrylate copolymers, very low density polyethylene (VLDPE) such as those available under the Flexomer® resin trade name from the Dow Chemical Co., Midland, Mich., styrene-ethylene-ethylene-propylene-styrene (SEEPS). These can also be used as the materials to be modified by the interpolymer to tailor their rheological properties.

As used herein, the term "VLDPE" refers to very low density polyethylene, which is a polyethylene with high levels of short chain branching with a typical density in the range of 0.880-0.915 g/cc. In many cases VLDPE is a substantially linear polymer. VLDPE is typically produced by copolymerization of ethylene with α-olefins. VLDPE is often produced using metallocene catalysts.

Unless otherwise specified, all molecular weight values are determined using gel permeation chromatography (GPC). Molecular weights are expressed as polyethylene equivalents with a relative standard deviation of 2.9% for the number average molecular weight ("Mn") and 5.0% for the weight average molecular weight ("Mw"). Unless otherwise indicated, the molecular weight values indicated herein are weight average molecular weights (Mw).

In some embodiments disclosed herein, the degree to which carbon monoxide is produced during the ODH process can be mitigated by converting it to carbon dioxide, which can then act as an oxidizing agent. The process can be manipulated so as to control the output of carbon dioxide from the process to a desired level. Using the methods described herein a user may choose to operate in carbon dioxide neutral conditions such that surplus carbon dioxide need not be flared or released into the atmosphere.

Disclosed herein are methods for mitigating carbon monoxide and/or acetylene formation in an ODH process and controlling the carbon dioxide output from the ODH process. Aspects of the methods include introducing, into at least one ODH reactor a gas mixture of a lower alkane, oxygen and carbon dioxide, under conditions that allow production of the corresponding alkene and smaller amounts of various by-products. For multiple ODH reactors, each reactor contains the same or different ODH catalyst, provided, in some embodiments, that at least one ODH catalyst is capable of using carbon dioxide as an oxidizing agent. In some embodiments steam or other inert diluents may also be introduced into the reactor as part of the gas mixture. In some embodiments the amount of carbon dioxide leaving the reactor is subsequently monitored. If the amount of carbon dioxide output is below a desired level then the amount of steam introduced into the reactor can be increased. If the amount of carbon dioxide output is above the desired level then the amount of steam introduced into the reactor can be decreased.

In some embodiments, the lower alkane is ethane, and the corresponding alkene is ethylene.

In further embodiments, at least one ODH reactor is a fixed bed reactor. In some embodiments at least one ODH reactor is a fixed bed reactor that includes heat dissipative particles within the fixed bed. In some embodiments the heat dissipative particles have a thermal conductivity that is greater than the catalyst. In alternative embodiments, at least one ODH reactor is a fluidized bed reactor.

In some embodiments, at least one ODH catalyst is a mixed metal oxide catalyst. In particular embodiments, at least one ODH catalyst is a mixed metal oxide of the formula: $Mo_aV_bTe_cNb_dPd_eO_f$, wherein a, b, c, d, e and f are the relative atomic amounts of the elements Mo, V, Te, Nb, Pd and O, respectively; and when a=1, b=0.01 to 1.0, c=0.01 to 1.0, d=0.01 to 1.0, 0.00≤e≤0.10 and f is a number to satisfy the valence state of the catalyst.

In other particular embodiments, at least one ODH catalyst is a mixed metal oxide of the formula:

$$Mo_{6.25-7.25}V_3O_d$$

where d is a number to satisfy the valence of the oxide.

Various embodiments relate to oxidative dehydrogenation (ODH) of lower alkanes into corresponding alkenes. Lower alkanes are saturated hydrocarbons with from 2 to 4 carbons, and the corresponding alkene includes hydrocarbons with the same number of carbons, but with one carbon to carbon double bond. While any of the lower alkanes can be converted to their corresponding alkenes using the methods disclosed herein, one particular embodiment is the ODH of ethane, producing its corresponding alkene, ethylene.

Carbon Dioxide Output

Carbon dioxide can be produced in the ODH reaction as a by-product of oxidation of the alkanes and recycled from the oxidation of carbon monoxide. Carbon dioxide can also be added into the ODH reactor when used as an inert diluent. Conversely, carbon dioxide may be consumed when it acts as an oxidant for the dehydrogenation reaction. The carbon dioxide output is therefore a function of the amount of carbon dioxide added and produced minus that consumed in the oxidative process. In some embodiments, the disclosed methods control the degree to which carbon dioxide acts as an oxidizing agent so as to impact the overall carbon dioxide output coming off the ODH reactor.

Measuring the amount of carbon dioxide coming off the ODH reactor can be done using any means known in the art. For example, one or more detectors such as GC, IR, or Rahman detectors, are situated immediately downstream of the reactor to measure the carbon dioxide output. While not required, the output of other components may also be measured. These include but are not limited to the amounts of ethylene, unreacted ethane, carbon monoxide and oxygen, and by-products such as acetic acid. Also, it should be noted that depending on the chosen metric for carbon dioxide output, the output levels of the other components, for example ethane, may actually be required.

Carbon dioxide output can be stated using any metric commonly used in the art. For example, the carbon dioxide output can be described in terms of mass flow rate (g/min) or volumetric flow rate ($cm^3$/min). In some embodiments, normalized selectivity can be used to assess the degree to which carbon dioxide is produced or consumed. In that instance, the net mass flow rate of $CO_2$—the difference between the mass flow rate of $CO_2$ entering and leaving the ODH reactor—is normalized to the conversion of ethane, in essence describing what fraction of ethane is converted into carbon dioxide as opposed to ethylene, or other by-products such as acetic acid. A carbon selectivity of 0 indicates that the amount of carbon dioxide entering the reactor is the same as the carbon dioxide output. In other words, the process is carbon dioxide neutral. A positive carbon dioxide selectivity alerts a user that carbon dioxide is being produced, and that any oxidation of carbon dioxide that is occurring is insufficient to offset that production, resulting in the process being carbon dioxide positive which may result in a lower selectivity for the olefin.

In some embodiments of the disclosure, product selectivity for carbon dioxide is less than about 10 wt. %, in some cases less than about 7.5 wt. % and in other cases less than about 5 wt. %. The product selectivity for carbon dioxide can be any of the values or range between any of the values recited above.

In some embodiments, the total amount of carbon dioxide in the stream exiting the one or more ODH reactors can be essentially the same as the total amount of carbon dioxide in the stream entering the one or more ODH reactors. In this instance, essentially the same means that the difference between the amount of carbon dioxide in the stream exiting the ODH reactors is within 2 weight percent (±2 wt. %) of the amount of carbon dioxide entering the ODH reactors. In particular embodiments of the disclosure, the amount of carbon dioxide in the stream exiting the ODH reactors can be about +5 wt. %, in some cases about +7.5 wt. % and in other cases about +10 wt. % and can be about −5 wt. %, in some cases about −7.5 wt. % and in other cases about −10 wt. % of the amount of carbon dioxide in the stream entering the ODH reactors. The difference between the amount of carbon dioxide in the stream exiting the ODH reactors and the amount of carbon dioxide entering the ODH reactors can be any value or range between any of the values recited above.

In some embodiments, the methods and apparatus disclosed herein provide the possibility of a carbon dioxide negative process. In this instance, carbon dioxide is oxidized at a higher rate than it is produced and shows a negative carbon selectivity. The ODH process may produce carbon dioxide, but the degree to which carbon dioxide is consumed while acting as an oxidizing agent offsets any production that is occurring. Many industrial processes, in addition to ODH, produce carbon dioxide which must be captured or flared where it contributes to the emission of greenhouse gases. When using a carbon dioxide negative process, the excess carbon dioxide from other processes may be captured and used as the inert diluent in the ODH process under conditions where there is negative carbon selectivity. An advantage then is the ability to reduce the amount of carbon dioxide produced in the ODH process in combination with other processes, such as thermal cracking. In addition, oxidation of carbon dioxide is endothermic and by increasing the degree to which carbon dioxide acts as an oxidizing agent, heat produced from ODH of ethane is partially offset by oxidation of carbon dioxide, reducing the degree to which heat must be removed from the reactor. In some embodiments, when acting as an oxidizing agent, carbon dioxide can produce carbon monoxide, which can be captured and used as an intermediate in production of other chemical products, such as methanol or formic acid.

In embodiments of a carbon dioxide negative process, the total amount of carbon dioxide in the stream exiting the one or more ODH reactors is less the total amount of carbon dioxide in the stream entering the one or more ODH reactors. In this instance, the difference between the amount of carbon dioxide in the stream exiting the ODH reactors is less than about 1 wt. %, in some circumstances less than about 2 wt. %, in other circumstances less than about 3 wt. %, in some cases less than bout 5 wt. %, in other cases less than about 7.5 wt. % and in some situations less than about 10 wt. % and can be higher, as a non-limiting example less than about 20 wt. % less than the amount of carbon dioxide in the stream entering the ODH reactors. The difference between the amount of carbon dioxide in the stream exiting the ODH reactors and the amount of carbon dioxide entering the ODH reactors can be any value or range between any of the values recited above.

The ODH Process

ODH of alkanes includes contacting a mixture of one or more alkanes and oxygen in an ODH reactor with an ODH catalyst under conditions that promote oxidation of the alkanes into their corresponding alkene. Conditions within the reactor are controlled by the operator and include, but are not limited to, parameters such as temperature, pressure, and flow rate. Conditions will vary and can be optimized for a particular alkane, or for a specific catalyst, or whether an inert diluent is used in the mixing of the reactants.

Use of an ODH reactor for performing an ODH process consistent with the disclosure falls within the knowledge of the person skilled in the art. For best results, the oxidative dehydrogenation of one or more alkanes may be conducted at temperatures from 300° C. to 450° C., or from 300° C. to 425° C., or from 330° C. to 400° C., at pressures from 0.5 to 100 psi (3.447 to 689.47 kPa), or from 15 to 50 psi (103.4 to 344.73 kPa), and the residence time of the one or more alkanes in the reactor may be from 0.002 to 30 seconds, or from 1 to 10 seconds.

In some embodiments, the process has a selectivity for the corresponding alkene (ethylene in the case of ethane ODH) of greater than 95%, or for example, greater than 98%. The gas hourly space velocity (GHSV) can be from 500 to 30000 $h^{-1}$, or greater than 1000 $h^{-1}$. In some embodiments, the space-time yield of corresponding alkene (productivity) in g/hour per kg of the catalyst can be at least 900 or above, or greater than 1500, or greater than 3000, or greater than 3500, at 350 to 400° C. In some embodiments, the productivity of the catalyst will increase with increasing temperature until the selectivity is decreased.

ODH Catalyst

Any of the ODH catalysts known in the art are suitable for use in the methods disclosed herein. Non-limiting examples of suitable oxidative dehydrogenation catalyst include those containing one or more mixed metal oxides selected from:

i) Catalysts of the Formula:

$$Mo_aV_bTe_cNb_dPd_eO_f$$

where a, b, c, d, e and f are the relative atomic amounts of the elements Mo, V, Te, Nb, Pd and O, respectively; and when a=1, b=0.01 to 1.0, c=0.01 to 1.0, d=0.01 to 1.0, 0.00≤e≤0.10 and f is a number to satisfy the valence state of the catalyst;

ii) Catalysts of the Formula:

$$Ni_gA_hB_iD_jO_f$$

where g is a number from 0.1 to 0.9, in many cases from 0.3 to 0.9, in other cases from 0.5 to 0.85, in some instances 0.6 to 0.8; h is a number from 0.04 to 0.9; i is a number from 0 to 0.5; j is a number from 0 to 0.5; and f is a number to satisfy the valence state of the catalyst; A is chosen from Ti, Ta, V, Nb, Hf, W, Y, Zn, Zr, Si and Al or mixtures thereof; B is chosen from La, Ce, Pr, Nd, Sm, Sb, Sn, Bi, Pb, Tl, In, Te, Cr, Mn, Mo, Fe, Co, Cu, Ru, Rh, Pd, Pt, Ag, Cd, Os, Ir, Au, Hg, and mixtures thereof; D is chosen from Ca, K, Mg, Li, Na, Sr, Ba, Cs, and Rb and mixtures thereof; and O is oxygen;

iii) Catalysts of the Formula:

$$Mo_aE_kG_lO_f$$

where E is chosen from Ba, Ca, Cr, Mn, Nb, Ta, Ti, Te, V, W and mixtures thereof; chosen from Bi, Ce, Co, Cu, Fe, K, Mg, V, Ni, P, Pb, Sb, Si, Sn, Ti, U, and mixtures thereof; a=1; k is 0 to 2; l=0 to 2, with the proviso that the total value of l for Co, Ni, Fe and mixtures thereof is less than 0.5; and f is a number to satisfy the valence state of the catalyst;

iv) Catalysts of the Formula:

$$V_mMo_nNb_oTe_pMe_qO_f$$

where Me is chosen from Ta, Ti, W, Hf, Zr, Sb and mixtures thereof; m is from 0.1 to 3; n is from 0.5 to 1.5; o is from 0.001 to 3; p is from 0.001 to 5; q is from 0 to 2; and f is a number to satisfy the valence state of the catalyst; and v) Catalysts of the Formula:

$$Mo_aV_rX_sY_tZ_uM_vO_f$$

where X is at least one of Nb and Ta; Y is at least one of Sb and Ni, Z is at least one of Te, Ga, Pd, W, Bi and Al; M is at least one of Fe, Co, Cu, Cr, Ti, Ce, Zr, Mn, Pb, Mg, Sn, Pt, Si, La, K, Ag and In; a=1.0 (normalized); r=0.05 to 1.0; s=0.001 to 1.0; t=0.001 to 1.0; u=0.001 to 0.5; v=0.001 to 0.3; and f is a number to satisfy the valence state of the catalyst.

When choosing a catalyst, those skilled in the art can appreciate that catalysts may vary with respective to selectivity and activity. Some embodiments of ODH of ethane in this disclosure use mixed metal oxide catalysts that can provide high selectivity to ethylene without significant loss in activity. Non-limiting example catalysts are those of the formula:

$$Mo_aV_bTe_cNb_dPd_eO_f$$

wherein a, b, c, d, e and f are the relative atomic amounts of the elements Mo, V, Te, Nb, Pd and O, respectively; and when a=1, b=0.01 to 1.0, c=0.01 to 1.0, d=0.01 to 1.0, 0.00≤e≤0.10 and f is a number to satisfy the valence state of the catalyst.

vi) a Mixed Metal Oxide Having the Empirical Formula:

$$Mo_{6.5-7.0}V_3O_d$$

where d is a number to satisfy the valence of the oxide.

vii) a Mixed Metal Oxide Having the Empirical Formula:

$$Mo_{6.25-7.25}V_3O_d$$

where d is a number to satisfy the valence of the oxide.

In some embodiments, the catalyst may be supported on/agglomerated with a binder. Some binders include acidic, basic or neutral binder slurries of $TiO_2$, $ZrO_2$ $Al_2O_3$, AlO(OH) and mixtures thereof. Another useful binder includes $Nb_2O_5$. The agglomerated catalyst may be extruded in a suitable shape (rings, spheres, saddles etc.) of a size typically used in fixed bed reactors. When the catalyst is extruded, various extrusion aids known in the art can be used. In some cases, the resulting support may have a cumulative surface area of less than 35 $m^2/g$ as measured by BET, in some cases, less than 20 $m^2/g$, in other cases, less than 3 $m^2/g$. and a cumulative pore volume from 0.05 to 0.50 $cm^3/g$.

ODH Reactor

Any of the known reactor types applicable for the ODH of alkanes may be used with the methods disclosed herein. In some embodiments, the methods may be used with conventional fixed bed reactors. In a typical fixed bed reactor, reactants are introduced into the reactor at one end, flow past an immobilized catalyst, products are formed and leave at the other end of the reactor. Designing a fixed bed reactor suitable for the methods disclosed herein can follow techniques known for reactors of this type. A person skilled in the art would know which features are required with respect to shape and dimensions, inputs for reactants, outputs for products, temperature and pressure control, and means for immobilizing the catalyst.

In some embodiments, the use of inert non-catalytic heat dissipative particles can be used within one or more of the ODH reactors. In various embodiments, the heat dissipative particles are present within the bed and include one or more non catalytic inert particulates having a melting point at least 30° C., in some embodiments at least 250° C., in further embodiments at least 500° C. above the temperature upper control limit for the reaction; a particle size in the range of 0.5 to 75 mm, in some embodiments 0.5 to 15, in further embodiments in the range of 0.5 to 8, in further embodiments in the range of 0.5 to 5 mm; and a thermal conductivity of greater than 30 W/mK (watts/meter Kelvin) within the reaction temperature control limits. In some embodiments the particulates are metal alloys and compounds having a thermal conductivity of greater than 50 W/mK (watts/meter Kelvin) within the reaction temperature control limits. Non-limiting examples of suitable metals that can be used in these embodiments include, but are not limited to, silver, copper, gold, aluminum, steel, stainless steel, molybdenum, and tungsten.

The heat dissipative particles can have a particle size of from about 1 mm to about 15 mm. In some embodiments, the particle size can be from about 1 mm to about 8 mm. The heat dissipative particles can be added to the fixed bed in an amount from 5 to 95 wt. %, in some embodiments from 30 to 70 wt. %, in other embodiments from 45 to 60 wt. % based on the entire weight of the fixed bed. The particles are employed to potentially improve cooling homogeneity and reduction of hot spots in the fixed bed by transferring heat directly to the walls of the reactor.

Additional embodiments include the use of a fluidized bed reactor, where the catalyst bed can be supported by a porous structure, or a distributor plate, located near a bottom end of the reactor and reactants flow through at a velocity sufficient to fluidize the bed (e.g. the catalyst rises and begins to swirl around in a fluidized manner). The reactants are converted to products upon contact with the fluidized catalyst and the reactants are subsequently removed from the upper end of the reactor. Design considerations those skilled in the art can modify and optimize include, but are not limited to, the shape of the reactor, the shape and size of the distributor plate, the input temperature, the output temperature, and reactor temperature and pressure control.

Embodiments of the disclosure include using a combination of both fixed bed and fluidized bed reactors, each with the same or different ODH catalyst. The multiple reactors can be arrayed in series or in parallel configuration, the design of which falls within the knowledge of the worker skilled in the art.

Oxygen/Alkane Mixture

Safety of the ODH process is a primary concern. For that reason, in many embodiments, mixtures of one or more alkanes with oxygen should be employed using ratios that fall outside of the flammability envelope of the one or more alkanes and oxygen. In some embodiments, the ratio of alkanes to oxygen may fall outside the upper flammability envelope. In these embodiments, the percentage of oxygen in the mixture can be less than 30 wt. %, in some cases less than 25 wt. %, or in other cases less than 20 wt. %, but greater than zero.

In embodiments with higher oxygen percentages, alkane percentages can be adjusted to keep the mixture outside of the flammability envelope. While a person skilled in the art would be able to determine an appropriate ratio level, in many cases the percentage of alkane is less than about 40 wt. % and greater than zero. As a non-limiting example, where the mixture of gases prior to ODH includes 20% oxygen and 40% alkane, the balance can be made up with an inert diluent. Non-limiting examples of useful inert diluents in this embodiment include, but are not limited to, one or more of nitrogen, carbon dioxide, and steam. In some embodiments, the inert diluent should exist in the gaseous state at the conditions within the reactor and should not increase the flammability of the hydrocarbon added to the reactor, characteristics that a skilled worker would understand when deciding on which inert diluent to employ. The inert diluent can be added to either of the alkane containing gas or the oxygen containing gas prior to entering the ODH reactor or may be added directly into the ODH reactor.

In embodiments of the disclosure, the volumetric feed ratio of oxygen to ethane ($O_2/C_2H_6$) provided to the one or more ODH reactors can be at least about 0.3, in some cases at least about 0.4, and in other cases at least about 0.5 and can be up to about 1, in some cases up to about 0.9, in other cases up to about 0.8, in some instances up to about 0.7 and in other instances up to about 0.6. The volumetric feed ratio of oxygen to ethane can be any of the values or range between any of the values recited above.

In some embodiments mixtures that fall within the flammability envelope may be employed, as a non-limiting example, in instances where the mixture exists in conditions that prevent propagation of an explosive event. In these non-limiting examples, the flammable mixture is created within a medium where ignition is immediately quenched. As a further non-limiting example, a user may design a reactor where oxygen and the one or more alkanes are mixed at a point where they are surrounded by a flame arresting material. Any ignition would be quenched by the surrounding material. Flame arresting materials include, but are not limited to, metallic or ceramic components, such as stainless steel walls or ceramic supports. In some embodiments, oxygen and alkanes can be mixed at a low temperature, where an ignition event would not lead to an explosion, then introduced into the reactor before increasing the temperature. The flammable conditions do not exist until the mixture is surrounded by the flame arrestor material inside of the reactor.

Carbon Monoxide Output

Carbon monoxide can be produced in the ODH reaction as a by-product of oxidation of the one or more alkanes. The carbon monoxide output is a function of the amount of carbon monoxide produced in the oxidative process.

Measuring the amount of carbon monoxide coming off the ODH reactor can be done using any means known in the art. For example, one or more detectors such as GC, IR, or Rahman detectors, are situated immediately downstream of the reactor to measure the carbon monoxide output. While not required, the output of other components may also be measured. These include but are not limited to the amounts of ethylene, unreacted ethane, acetylene, carbon dioxide and oxygen, and by-products such as acetic acid.

Carbon monoxide output can be stated using any metric commonly used in the art. For example, the carbon monoxide output can be described in terms of mass flow rate (g/min) or volumetric flow rate ($cm^3/min$). In some embodiments, normalized selectivity can be used to assess the degree to which carbon monoxide is produced or consumed. In that instance the net mass flow rate of CO—the difference between the mass flow rate of CO leaving the ODH reactor—is normalized to the conversion of ethane, in essence describing what fraction of ethane is converted into carbon monoxide as opposed to ethylene, or other by-products such as acetic acid.

Many industrial processes, in addition to ODH, produce carbon monoxide which must be captured or flared where it contributes to the emission of greenhouse gases. Using the carbon monoxide mitigation steps disclosed herein converts most, if not all, carbon monoxide resulting from the ODH process to carbon dioxide. An advantage then is the ability to reduce or eliminate the amount of carbon monoxide produced in the ODH process in combination with other processes, such as thermal cracking.

Acetylene Output

Acetylene can be produced in the ODH reaction as a by-product of oxidation of the one or more alkanes. The acetylene output is a function of the amount of acetylene produced in the oxidative process.

Measuring the amount of acetylene coming off the ODH reactor can be done using any means known in the art. For example, one or more detectors such as GC, IR, or Rahman detectors, are situated immediately downstream of the reactor to measure the acetylene output. While not required, the output of other components may also be measured. These include but are not limited to the amounts of ethylene, unreacted ethane, carbon monoxide, carbon dioxide and oxygen, and by-products such as acetic acid.

Acetylene output can be stated using any metric commonly used in the art. For example, the acetylene output can be described in terms of mass flow rate (g/min), volumetric flow rate ($cm^3$/min) or volumetric parts per million (vppm). In some embodiments, normalized selectivity can be used to assess the degree to which acetylene is produced or consumed. In that instance the net mass flow rate of acetylene—the difference between the mass flow rate of acetylene leaving the ODH reactor—is normalized to the conversion of ethane, in essence describing what fraction of ethane is converted into acetylene as opposed to ethylene, or other by-products such as acetic acid.

Using the acetylene mitigation steps disclosed herein reacts most, if not all, acetylene resulting from the ODH process. An advantage then is the ability to reduce or eliminate the amount of acetylene produced in the ODH process in combination with other processes, such as thermal cracking and eliminate downstream unit operations in an ODH-type process.

Addition of Steam

The amount of steam added to the ODH process affects the degree to which carbon dioxide acts as an oxidizing agent. In some embodiments steam may be added directly to the ODH reactor, or steam may be added to the individual reactant components—the lower alkane, oxygen, or inert diluent—or combinations thereof, and subsequently introduced into the ODH reactor along with one or more of the reactant components. Alternatively, steam may be added indirectly as water mixed with either the lower alkane, oxygen or inert diluent, or a combination thereof, with the resulting mixture being preheated before entering the reactor. When adding steam indirectly as water the preheating process should increase the temperature so that the water is entirely converted to steam before entering the reactor.

Increasing the amount of steam added to a reactor increases the degree to which carbon dioxide acts as an oxidizing agent. Decreasing the amount of steam added to the reactor decreases the degree to which carbon dioxide acts as an oxidizing agent. In some embodiments a user monitors the carbon dioxide output and compares it to a predetermined target carbon dioxide output. If the carbon dioxide output is above the target a user can then increase the amount of steam added to the ODH process. If the carbon dioxide output is below the target a user can decrease the amount of steam added to the ODH process, provided steam has been added. Setting a target carbon dioxide output level is dependent on the requirements for the user. In some embodiments increasing the steam added will have the added effect of increasing the amount of acetic acid and other by-products produced in the process. A user that is ill equipped to separate out larger amounts of acetic acid from the output of the ODH may instead reduce steam levels to a minimum, while a user that desires a process that consumes carbon dioxide may choose to maximize the amount of steam that can be added.

In embodiments of the disclosure, the amount of steam added to the one or more ODH reactors can be up to about 50 wt. %, in some circumstances up to about 40 wt. %, in some cases up to about 35 wt. %, in other cases up to about 30 wt. %, and in some instances up to about 25 wt. % and can be zero, in some cases at least 0.5 wt. %, in other cases at least 1 wt. %, in other cases at least 5 wt. %, in some instances at least 10 wt. % and in other instances at least 15 wt. % of the stream entering the one or more ODH reactors. The amount of steam in the stream entering the one or more ODH reactors can be any value or range between any of the values recited above.

In some embodiments when using two or more ODH reactors a user may choose to control carbon dioxide output in only one, or less than the whole complement of reactors. For example, a user may opt to maximize carbon dioxide output of an upstream reactor so that the higher level of carbon dioxide can be part of the inert diluent for the subsequent reactor. In that instance, maximizing carbon dioxide output upstream minimizes the amount of inert diluent that would need to be added to the stream prior to the next reactor.

There is no requirement for adding steam to an ODH process, as it is one of many alternatives for the inert diluent. For processes where no steam is added, the carbon dioxide output is maximized under the conditions used with respect to ethane, oxygen and inert diluent inputs. Decreasing the carbon dioxide output can then be a matter of adding steam to the reaction until carbon dioxide output drops to the desired level. In embodiments where oxidative dehydrogenation conditions do not include addition of steam, and the carbon dioxide output is higher than the desired carbon dioxide target level, steam may be introduced into the reactor while keeping relative amounts of the main reactants and inert diluent—lower alkane, oxygen and inert diluent—added to the reactor constant, and monitoring the carbon dioxide output, increasing the amount of steam until carbon dioxide decreases to the target level.

In some embodiments, a carbon dioxide neutral process can be achieved by increasing steam added so that any carbon dioxide produced in the oxidative dehydrogenation process can then be used as an oxidizing agent such that there is no net production of carbon dioxide. Conversely, if a user desires net positive carbon dioxide output then the amount of steam added to the process can be reduced or eliminated to maximize carbon dioxide production. As the carbon dioxide levels increase there is potential to reduce oxygen consumption, as carbon dioxide is competing as an oxidizing agent. The skilled person would understand that using steam to increase the degree to which carbon dioxide acts as an oxidizing agent can impact oxygen consumption. The implication is that a user can optimize reaction conditions with lower oxygen contributions, which may assist in keeping mixtures outside of flammability limits.

In embodiments of the invention, the stream exiting the one or more ODH reactors can be treated to remove or separate water and water soluble hydrocarbons from the stream exiting the one or more ODH reactors. In particular embodiments, this stream is fed to the second reactor.

Acetic Acid Removal

Prior to being fed to the second reactor, the stream exiting the one or more ODH reactors is directed to quench tower or acetic acid scrubber, which facilitates removal of oxygenates, such as acetic acid, and water via a bottom outlet. A stream containing unconverted lower alkane (such as ethane), corresponding alkene (such as ethylene), unreacted oxygen, carbon dioxide, carbon monoxide, optionally acetylene and inert diluent, are allowed to exit the scrubber and are fed to the second reactor.

The oxygenates removed via the quench tower or acetic acid scrubber can include carboxylic acids (for example acetic acid), aldehydes (for example acetaldehyde) and ketones (for example acetone). The amount of oxygenate compounds remaining in the stream exiting the scrubber and fed to the second reactor will often be zero, i.e, below the detection limit for analytical test methods typically used to detect such compounds. When oxygenates can be detected they can be present at a level of up to about 1 per million by volume (ppmv), in some cases up to about 5 ppmv, in other cases less than about 10 ppmv, in some instances up to about 50 ppmv and in other instances up to about 100 ppmv and can be present up to about 2 vol. %, in some cases up to about 1 vol. %, and in other cases up to about 1,000 ppmv. The amount of oxygenates or acetic acid in the stream exiting the scrubber and fed to the second reactor can be any value, or range between any of the values recited above.

The Second Reactor

In many embodiments, the ODH reactor (or reactors) can provide a stream containing at least a small amount of oxygen remaining as reactor effluent. In embodiments of the disclosure, the oxygen can provide a benefit to the ODH reactor product gas. In some embodiments, when the ODH catalyst is exposed to an oxygen free reducing environment at elevated temperature, it may become permanently degraded. In other embodiments, if the level of oxygen in the product gas from the ODH reactor contains less than about 1 ppm of oxygen, most, if not all, of the one or more alkanes are converted to one or more alkenes in the inlet portion of the reactor and a large portion of the reactor catalyst bed is not utilized.

In other embodiments, oxygen in the ODH reactor product gas causes serious safety and operational issues in the downstream equipment, as a non-limiting example, at the first compression stage of an ODH process. This process safety consideration presents a need to remove oxygen to a very low or non-detectable level before the product gas is compressed.

One method used to reduce/eliminate oxygen in the ODH product gas focuses on catalytically combusting a small portion of the ODH product gas to the complete consumption of any residual oxygen. This approach is viable, however, in many cases it is undesirable, because it increases the overall oxygen consumption in the ODH process and, in the non-limiting example of the alkane being ethane, reduces overall process selectivity toward ethylene.

This disclosure describes a process where the ODH reaction can proceed with partial consumption of $CO_2$ ($CO_2$ can act as an oxidizing agent, and be converted to CO), reducing overall oxygen consumption in the process by providing a portion of the required oxygen from $CO_2$. In many embodiments, more oxygen passes through the catalyst bed unconverted when $CO_2$ is provided and acts as an oxidizing agent.

Oxidation of Carbon Monoxide

In the process of this disclosure, the ODH reactor product stream is fed to the second reactor, which contains a catalyst that includes one or more selected from a group 11 metal, a group 4 metal, a group 7 metal, a group 9 metal, a lanthanide metal, and an actinide metal and/or their corresponding metal oxides capable of converting at least a portion of the carbon monoxide to carbon dioxide. The carbon dioxide can be recycled to the ODH reactor to act as an oxidizing agent as described above.

In embodiments of the disclosure, the group 11 metal can be selected from copper, silver, gold and combinations thereof. In certain embodiments of the disclosure, the group 11 metal is silver or copper.

In embodiments of the disclosure, the group 4 metal can be selected from titanium, zirconium, hafnium, rutherfordium and combinations thereof. In certain embodiments of the disclosure, the group 4 metal is zirconium.

In embodiments of the disclosure, the group 7 metal can be selected from manganese, technetium, rhenium, bohrium and combinations thereof. In certain embodiments of the disclosure, the group 7 metal is manganese.

In embodiments of the disclosure, the group 9 metal can be selected from cobalt, rhodium, iridium, meiternium and combinations thereof. In certain embodiments of the disclosure, the group 9 metal is cobalt.

In embodiments of the disclosure, the lanthanide metal can be selected from La, Ce, Pr, Nd, Pm, Sm, Eu, Gd, Tb, Dy, ho, Er, Tm, Yb and combinations thereof. In certain embodiments of the disclosure, the lanthanide metal is Cerium.

In embodiments of the disclosure, the actinide metal can be selected from Ac, Th, Ps, U, Np, Pu, Am, Cm, Bk, Cf, Es, Fm, Md, No and combinations thereof. In certain embodiments of the disclosure, the actinide metal is thorium.

In embodiments of the disclosure, the second reactor catalyst, in some cases a group 11 metal, is used in conjunction with a promoter. In many embodiments, the promoter is selected from one or more of the lanthanide and actinide metals (as defined above) and their corresponding metal oxides. In certain embodiments, the promoter is selected from one or more of the lanthanide metals and their corresponding metal oxides. In particular embodiments, the promoter includes cerium and its corresponding metal oxides.

In embodiments of the disclosure, the second reactor catalyst, in some cases a group 11 metal, and optional promotor are provided on a support. The support is typically an inert solid with a high surface area, to which the second reactor catalyst and optional promotor can be affixed. In many embodiments, the support includes Si, Ge, Sn, their corresponding oxides and combinations thereof.

In embodiments of the disclosure, non-limiting examples of suitable second reactor catalysts with optional promotors and supports include $Ag/SiO_2$, $AgCeO_2/SiO_2$, $AgZrO_2/SiO_2$, $AgCo_3O_4/SiO_2$, $Cu/SiO_2$, $CuCeO_2/SiO_2$, $CuZrO_2/SiO_2$, $CuCo_3O_4/SiO_2$ and combinations thereof.

In other embodiments of the disclosure, non-limiting examples of suitable second reactor catalysts with optional promotors and supports include $AgCeO_2/SiO_2$, $AgZrO_2/SiO_2$ and combinations thereof.

In specific embodiments of the disclosure, the second reactor catalyst includes silver, the optional promoter includes cerium and the support includes $SiO_2$.

In specific embodiments of the disclosure, the second reactor catalyst includes copper, the optional promoter includes cerium and the support includes $SiO_2$.

In specific embodiments of the disclosure, when oxidation of carbon monoxide is preferentially desired, the second reactor catalyst includes manganese, the optional promoter includes cerium and the support includes $SiO_2$.

In embodiments of the disclosure, the group 11 metal with optional promoter and optional support can be used in a process where 1) some oxygen is in the stream leaving the ODH reactor; 2) the temperature in the stream is decreased; 3) the cooled stream is fed to an acetic acid scrubber; 4) the stream from the acetic acid scrubber is fed to reactor 2 as described above, where most or all of the residual $O_2$ is consumed and CO is converted to $CO_2$; and 5) optionally, the $CO_2$ is recycled back to the ODH reactor.

In embodiments of the disclosure, the amount of oxygen in the stream leaving the ODH reactor in 1) can be at least about 80 ppm, in some cases at least about 100 ppm, in other cases at least about 150 ppm and in some instances at least about 200 ppm and can be up to about 5 wt. %, in some cases up to about 4 wt %, in other cases up to about 3 wt. %, in some instances up to about 2 wt. %, in other instances up to about 1 wt. %, and in particular situations up to about 500 ppm. The amount of oxygen in the stream leaving the ODH reactor in 1) can be any of the values or range between any of the values recited above.

In embodiments of the disclosure, when there is oxygen in the stream leaving the second reactor (in some instances the amount of oxygen will be undetectable or zero ppm), the amount of oxygen in the stream leaving the second reactor can be at least about 1 ppm, in some cases at least about 2 ppm, in other cases at least about 3 ppm and in some instances at least about 5 ppm and can be up to about 1 wt. %, in some cases up to about 0.9 wt. %, in other cases up to about 0.8 wt. %, in some instances up to about 0.7 wt. %, in other instances up to about 0.6 wt. %, and in particular situations up to about 0.5 wt. %. The amount of oxygen in the stream leaving the second reactor can be any of the values or range between any of the values recited above.

In embodiments of the disclosure, the amount of carbon monoxide in the stream leaving the ODH reactor in 1) can be at least about 100 ppm, in some cases at least about 200 ppm, in other cases at least about 300 ppm and in some instances at least about 400 ppm and can be up to about 10 wt. %, in some cases up to about 9 wt. %, in other cases up to about 8 wt. %, in some instances up to about 7 wt %, in other instances up to about 6 wt. %, and in particular situations up to about 5 wt. %. The amount of carbon monoxide in the stream leaving the ODH reactor in 1) can be any of the values or range between any of the values recited above.

In embodiments of the disclosure, when there is carbon monoxide in the stream leaving the second reactor (in some instances the amount of carbon monoxide will be undetectable or zero ppm), the amount of carbon monoxide in the stream leaving the second reactor can be at least about 1 ppm, in some cases at least about 2 ppm, in other cases at least about 3 ppm and in some instances at least about 5 ppm and can be up to about 8 wt. %, in some cases up to about 7 wt. %, in other cases up to about 6 wt. %, in some instances up to about 5 wt. %, in other instances up to about 4 wt. %, and in particular situations up to about 3 wt. %. The amount of carbon monoxide in the stream leaving the second reactor can be any of the values or range between any of the values recited above.

In embodiments of the disclosure, temperature in the second reactor can be at least about 40, in some cases at least about 45, in other cases at least about 50 and in some instances at least about 55° C. and can be up to about 200, in some instances up to about 150, in other instances up to about 120, in some circumstances up to about 90, in some cases up to about 85, in other cases up to about 80, in some instances up to about 75 and in other instances up to about 70° C. The temperature of second reactor can be any temperature value or range between any of the temperature values, including a temperature gradient within the second reactor, recited above.

Acetylene Elimination

In the process of this disclosure, the ODH reactor product stream is fed to the second reactor, which contains a catalyst that includes one or more selected from a group 11 metal, a group 4 metal, a group 9 metal, a lanthanide metal, and an actinide metal and/or their corresponding metal oxides capable of reacting at least a portion of the acetylene.

In embodiments of the disclosure, the group 11 metal can be selected from copper, silver, gold and combinations thereof. In certain embodiments of the disclosure, the group 11 metal is silver.

In embodiments of the disclosure, the group 4 metal can be selected from titanium, zirconium, hafnium, rutherfordium and combinations thereof. In certain embodiments of the disclosure, the group 4 metal is zirconium.

In embodiments of the disclosure, the group 9 metal can be selected from cobalt, rhodium, iridium, meiternium and combinations thereof. In certain embodiments of the disclosure, the group 9 metal is cobalt.

In embodiments of the disclosure, the lanthanide metal can be selected from La, Ce, Pr, Nd, Pm, Sm, Eu, Gd, Tb, Dy, ho, Er, Tm, Yb and combinations thereof. In certain embodiments of the disclosure, the lanthanide metal is Cerium.

In embodiments of the disclosure, the actinide metal can be selected from Ac, Th, Ps, U, Np, Pu, Am, Cm, Bk, Cf, Es, Fm, Md, No and combinations thereof. In certain embodiments of the disclosure, the actinide metal is thorium.

In embodiments of the disclosure, the second reactor catalyst, in some cases a group 11 metal, is used in conjunction with a promoter. In many embodiments, the promoter is selected from one or more of the lanthanide and actinide metals (as defined above) and their corresponding metal oxides. In certain embodiments, the promoter is selected from one or more of the lanthanide metals and their corresponding metal oxides. In particular embodiments the promoter includes cerium and its corresponding metal oxides.

In embodiments of the disclosure, the second reactor catalyst, in some cases a group 11 metal, and optional promotor are provided on a support. The support is typically an inert solid with a high surface area, to which the second reactor catalyst and optional promotor can be affixed. In many embodiments, the support includes Si, Ge, Sn, their corresponding oxides and combinations thereof.

In embodiments of the disclosure, non-limiting examples of suitable second reactor catalysts with optional promotors and supports include $Ag/SiO_2$, $AgCeO_2/SiO_2$, $AgZrO_2/SiO_2$, $AgCo_3O_4/SiO_2$, $Cu/SiO_2$, $CuCeO_2/SiO_2$, $CuZrO_2/SiO_2$, $CuCo_3O_4/SiO_2$ and combinations thereof.

In other embodiments of the disclosure, non-limiting examples of suitable second reactor catalysts with optional promotors and supports include $AgCeO_2/SiO_2$, $AgZrO_2/SiO_2$ and combinations thereof.

In specific embodiments of the disclosure, the second reactor catalyst includes silver, the optional promoter includes cerium and the support includes $SiO_2$.

In specific embodiments of the disclosure, the second reactor catalyst includes copper, the optional promoter includes cerium and the support includes $SiO_2$.

In embodiments of the disclosure, the group 11 metal with optional promoter and optional support can be used in a process where 1) some acetylene is in the stream leaving the ODH reactor; 2) the temperature in the stream is decreased; 3) the cooled stream is fed to an acetic acid scrubber; 4) the stream from the acetic acid scrubber is fed to reactor 2 as described above, where most or all of the acetylene is consumed and CO is oxidized to $CO_2$; and 5) optionally, the $CO_2$ is recycled back to the ODH reactor.

In embodiments of the disclosure, when there is acetylene in the stream leaving the ODH reactor (in some instances the amount of acetylene will be undetectable or zero vppm), the amount of acetylene in the stream leaving the ODH reactor in 1) can be at least about 1 vppm, in some cases at least about 2 vppm, in other cases at least about 5 vppm and in some instances at least about 10 vppm and can be up to about 1000 vppm, in some cases up to about 750 vppm, in other cases up to about 500 vppm, in some instances up to about 400 vppm, in other instances up to about 300 vppm, and in particular situations up to about 300 vppm. The amount of acetylene in the stream leaving the ODH reactor in 1) can be any of the values or range between any of the values recited above.

In embodiments of the disclosure, the amount of acetylene in the stream leaving the second reactor will be less than the amount entering the second reactor and, in many instances, the stream exiting the second reactor will be substantially free of acetylene.

In embodiments of the disclosure, when there is acetylene in the stream leaving the second reactor (in many instances the amount of acetylene will be undetectable, less than 1 vppm, or zero vppm), the amount of acetylene in the stream leaving the second reactor can be at least about 1 vppm, in some cases at least about 2 vppm, in other cases at least about 3 vppm and in some instances at least about 5 vppm and can be up to about 100 vppm, in some cases up to about 50 vppm, in other cases up to about 25 vppm, in some instances up to about 20 vppm, in other instances up to about 15 vppm, and in particular situations up to about 10 vppm. The amount of acetylene in the stream leaving the second reactor can be any of the values or range between any of the values recited above.

In embodiments of the disclosure, temperature in the second reactor can be at least about 40, in some cases at least about 45, in other cases at least about 50 and in some instances at least about 55° C. and can be up to about 200, in some instances up to about 150, in other instances up to about 120, in some circumstances up to about 90, in some cases up to about 85, in other cases up to about 80, in some instances up to about 75 and in other instances up to about 70° C. The temperature of second reactor can be any temperature value or range between any of the temperature values, including a temperature gradient within the second reactor, recited above.

In embodiments of the disclosure, the stream from the ODH reactor is cooled to a lower temperature prior to being fed to an acetic acid scrubber (as described below). The temperature of the stream prior to entering the acetic acid scrubber can be at least about 40, in some cases at least about 45, and in other cases at least about 50° C. and can be up to about 90, in some cases up to about 85, in other cases up to about 80, in some instances up to about 75 and in other instances up to about 70° C. The temperature of the ODH reactor product stream fed to an acetic acid scrubber can be cooled to any temperature value or range between any of the temperature values recited above.

In embodiments of the disclosure, the configuration described above can allow for the size of the air separation plant to be reduced, as well as improving the life of the ODH catalyst, by allowing it to be exposed to an oxygen containing environment at all times. In additional embodiments, the configuration described above can improve the reliability and safety of the ODH reactor and downstream equipment.

In embodiments of the disclosure, the net $CO_2$ generation in the process described herein can be optimized to be zero. In these embodiments, the need to flare off any $CO_2$ (with some amount of alkane/alkene) from the $CO_2$-recyle loop as described herein. In these embodiments, the total process yield of alkane to alkene can be improved.

ODH Complex

In the following description of the present disclosure for reference to the figures it should be noted that like parts are designated by like reference numbers.

In embodiments of the disclosure, the chemical complex of the present disclosure, shown in one embodiment schematically in FIG. 1, includes, in cooperative arrangement, an ODH reactor 10, a quench tower or acetic acid scrubber 20, a second reactor 25 (as described herein), an amine wash tower 30, a drier 40, a distillation tower 50, and an oxygen separation module 60. ODH reactor 10 includes an ODH catalyst capable of catalyzing, in the presence of oxygen which may be introduced via oxygen line 70, the oxidative dehydrogenation of alkanes introduced via alkane line 80. Although second reactor 25 is shown directly after quench tower or acetic acid scrubber 20, it can be placed further downstream. In many cases, the process configuration can be more energy efficient if second reactor 25 is placed after the input stream has been compressed.

The ODH reaction may also occur in the presence of an inert diluent, such as carbon dioxide, nitrogen, or steam, that is added to ensure the mixture of oxygen and hydrocarbon are outside of flammability limits. Determination of whether a mixture is outside of the flammability limits, for the prescribed temperature and pressure, is within the knowledge of the skilled worker. An ODH reaction that occurs within ODH reactor 10 may also produce, depending on the catalyst and the prevailing conditions within ODH reactor 10, a variety of other products which may include carbon dioxide, carbon monoxide, oxygenates, and water. These products leave ODH reactor 10, along with unreacted alkane, corresponding alkene, residual oxygen, carbon monoxide and inert diluent, if added, via ODH reactor product line 90.

ODH reactor product line 90 is directed to quench tower or acetic acid scrubber 20 which quenches the products from product line 90 and facilitates removal of oxygenates and water via quench tower bottom outlet 100. Unconverted lower alkane, corresponding alkene, unreacted oxygen, carbon dioxide, carbon monoxide, and inert diluent added to quench tower 20 exit through quench tower overhead line 110 and are directed into second reactor 25.

Second reactor 25 contains the group 11 metal with optional promoter and optional support as described above, which causes unreacted oxygen to react with carbon monoxide to form carbon dioxide or, optionally, reacts acetylene to reduce or eliminate it. In second reactor 25, most or all of the unreacted oxygen and acetylene is consumed. All or a portion of the carbon dioxide in reactor 25 can be recycled back to ODH reactor 10 via recycle lines 27 and 220 to act as an oxidizing agent as described above. The remaining unconverted lower alkane, corresponding alkene, unreacted oxygen (if present), all or part of the carbon dioxide, carbon monoxide (if present), and inert diluent are conveyed to amine wash tower 30 via line 115.

Any carbon dioxide present in line 115 is isolated by amine wash tower 30 and captured via carbon dioxide bottom outlet 120 and may be sold, or, alternatively, may be recycled back to ODH reactor 10 as described above. Constituents introduced into amine wash tower 30 via line 115, other than carbon dioxide, leave amine wash tower 30 through amine wash tower overhead line 130 and are passed through a dryer 40 before being directed to distillation tower 50, where C2/C2+ hydrocarbons are isolated and removed via C2/C2+ hydrocarbons bottom outlet 150. The remainder includes mainly C1 hydrocarbons, including remaining inert diluent and carbon monoxide (if any), which leave distillation tower 50 via overhead stream 160 and is directed to oxygen separation module 60.

Oxygen separation module 60 includes a sealed vessel having a retentate side 170 and a permeate side 180, separated by oxygen transport membrane 190. Overhead stream 16 may be directed into either of retentate side 170 or permeate side 180. Optionally, a flow controlling means 260 (FIG. 3D) may be included that allows for flow into both sides at varying levels. In that instance an operator may choose what portion of the flow from overhead stream 160 enters retentate side 170 and what portion enters permeate side 180. Depending upon conditions an operator may switch between the two sides, to allow equivalent amounts to enter each side, or bias the amount directed to one of the two sides. Oxygen separation module 60 also includes air input 200 for the introduction of atmospheric air, or other oxygen containing gas, into the retentate side 170. Combustion of products introduced into retentate side 170, due to the introduction of oxygen, may contribute to raising the temperature of oxygen transport membrane 190 to at least about 850° C. so that oxygen can pass from retentate side 170 to permeate side 180. Components within the atmospheric air, or other oxygen containing gas, other than oxygen, cannot pass from retentate side 170 to permeate side 180 and can only leave oxygen separation module 60 via exhaust 210.

As a result of oxygen passing from retentate side 170 to permeate side 180, there is separation of oxygen from atmospheric air, or other oxygen containing gas, introduced into retentate side 170. The result is production of oxygen enriched gas on permeate side 180, which is then directed via oxygen enriched bottom line 220 to ODH reactor 10, either directly or in combination with oxygen line 70 (as shown in FIG. 1). When overhead stream 160 is directed into retentate side 170 the degree of purity of oxygen in oxygen enriched bottom line 220 can approach 99%. Conversely, when overhead stream 160 is directed into permeate side 180 the degree of purity of oxygen in oxygen enriched bottom line 220 is lower, with an upper limit ranging from 80%-90% oxygen, the balance in the form of carbon dioxide, water, and remaining inert diluent, all of which do not affect the ODH reaction as contemplated by the present disclosure and can accompany the enriched oxygen into ODH reactor 10. Water and carbon dioxide can be removed by quench tower 20 and amine wash tower 30, respectively. In some embodiments of the disclosure, some or all of the carbon dioxide can be captured for sale as opposed to being flared where it contributes to greenhouse gas emissions. In other embodiments, when carbon dioxide is used in the ODH process, any carbon dioxide captured in the amine wash can be recycled back to ODH reactor 10.

Oxygen transport membrane 190 is temperature dependent, only allowing transport of oxygen when the temperature reaches at least about 850° C. In some embodiments, the components in overhead stream 160 by themselves are not capable, upon combustion in the presence of oxygen, to raise the temperature of oxygen transport membrane 190 to the required level. In this embodiment, the chemical complex of the present disclosure also includes fuel enhancement line 230, upstream of oxygen separation module 60, where combustible fuel, as a non-limiting example methane, may be added to supplement the combustible products from overhead stream 160.

Figure 3A:
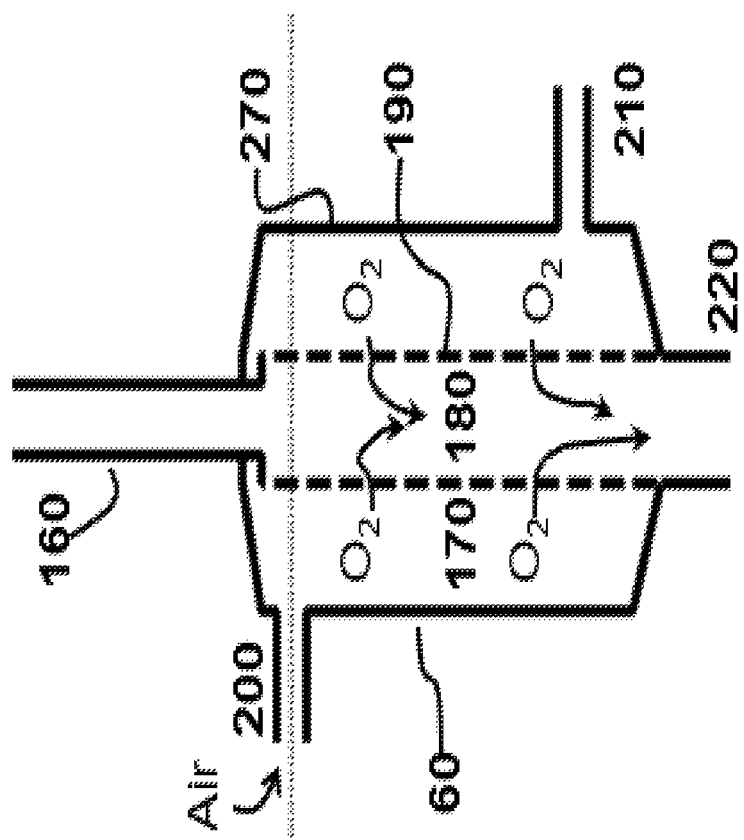
FIG. 3A—Schematic of embodiment of oxygen separation module where C1 hydrocarbon containing line is directed to permeate side.
Figure 3B:
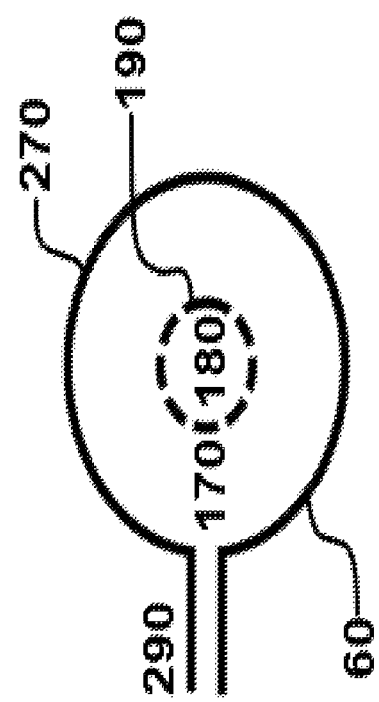
FIG. 3B—Cross section of oxygen separation module through dotted line present in FIGS. 3A, C, and D.
Figure 3C:
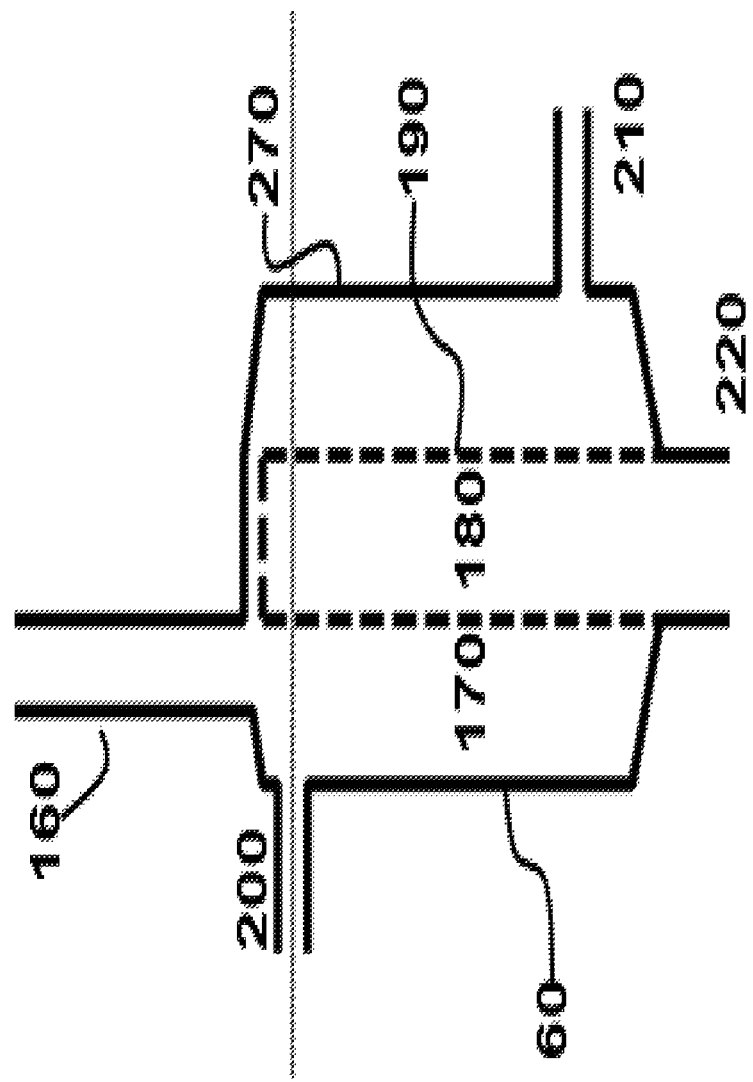
FIG. 3C—Schematic of embodiment of oxygen separation module where C1 hydrocarbon containing line is directed to the retentate side.

In an embodiment of the disclosure, the oxygen separation module 60 is a tube, as depicted schematically in FIG. 3B. The oxygen transport membrane 190 can be a tube and can fit inside a larger tube 270 which forms the outer wall of oxygen separation module 60. The annular space between the larger tube 270 and oxygen transport membrane 190 corresponds to the retentate side, while the space within oxygen transport membrane 190 corresponds to the permeate side. Material suitable for construction of the outer wall include those resistant to temperatures that exceed 850° C. and approach 1000° C., selection of which falls within the knowledge of the skilled worker.

Figure 3D:
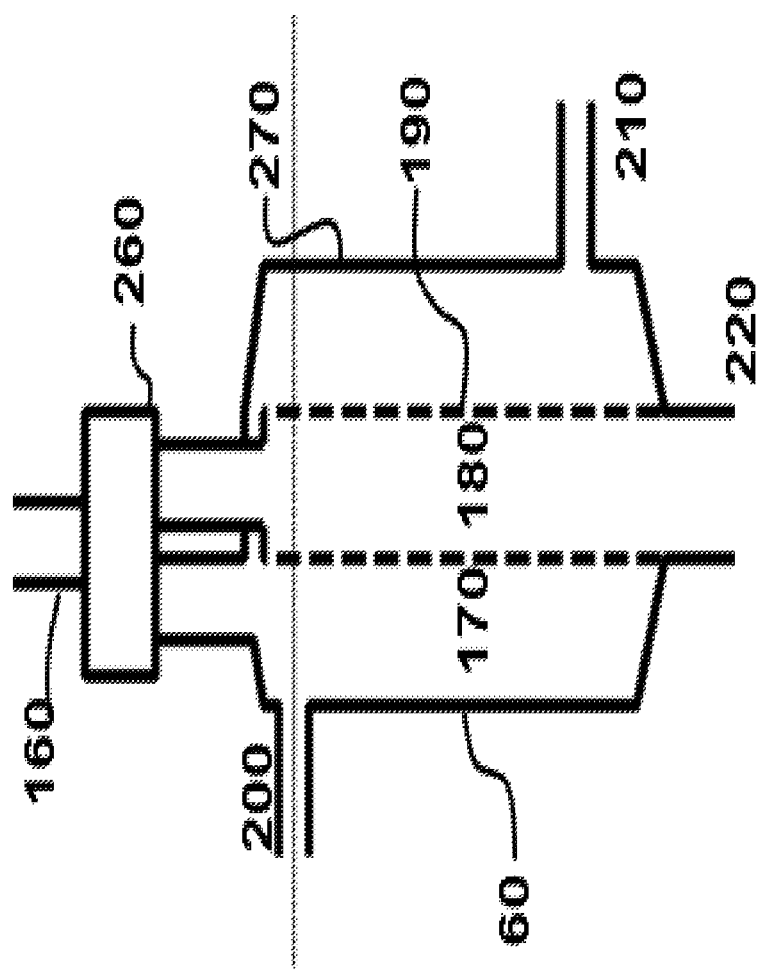
FIG. 3D—Schematic of embodiment of oxygen separation module where C1 hydrocarbon containing line can be directed to either of or both the permeate side and the retentate side.

The present disclosure contemplates the inlet for the overhead stream 160 entering the oxygen transport module 60 into either of the permeate side (FIG. 3A) or the retentate side (FIG. 3B). In some embodiments, oxygen separation module 60 can have C1 hydrocarbon containing line directed to the retentate side 180. The present disclosure also contemplates the use of a valve 260 for switching between directing the overhead stream 160 to the retentate side 180 or the permeate side 170 (FIG. 3D). This would allow an operator to choose which of the sides, permeate or retentate, that the overhead stream is directed to.

In embodiments of the disclosure, a concern for ODH processes is the mixing of a hydrocarbon with oxygen. Under certain conditions the mixture may be unstable and lead to an explosive event. U.S. Published Patent Application No. 2018/0009662 ('662 application) published Jan. 11, 2018, titled "Inherently Safe Oxygen/Hydrocarbon Gas Mixer", discloses a means to mix a hydrocarbon containing gas with an oxygen containing gas in a flooded mixing vessel. By mixing in this way pockets of unstable compositions are surrounded by a non-flammable liquid so that even if an ignition event occurred it would be quenched immediately. Provided addition of the gases to the ODH reaction is controlled so that homogeneous mixtures fall outside of the flammability envelope, for the prescribed conditions with respect to temperature and pressure, the result is a safe homogeneous mixture of hydrocarbon and oxygen. The present disclosure may be supplemented with a flooded gas mixer as described in the '662 application.

Figure 2:
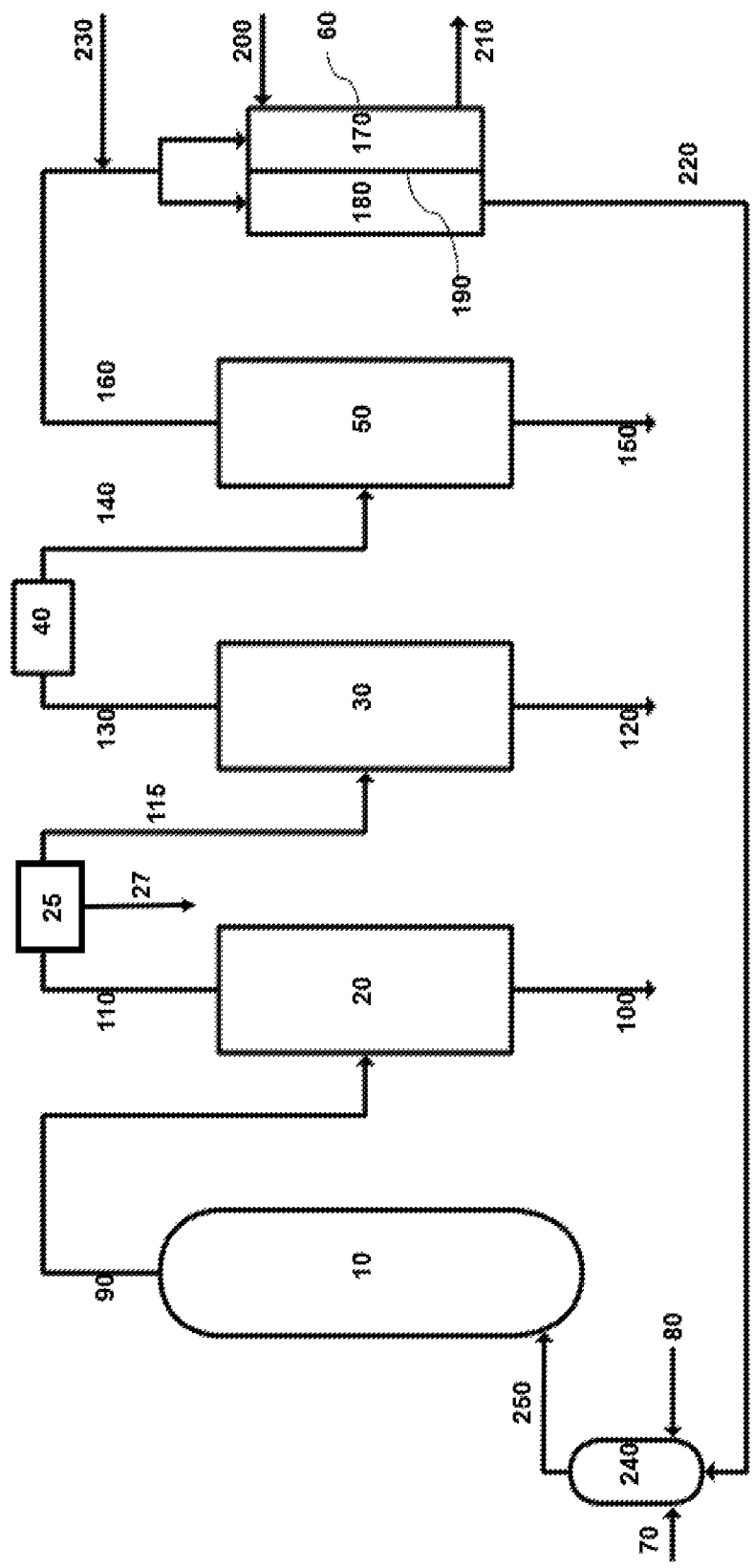
FIG. 2 is a graphic depiction of a chemical complex according to some embodiments of the disclosure.

In one embodiment of the disclosure, there is a flooded gas mixer 240 (FIG. 2) upstream of ODH reactor 10. In this instance oxygen line 70 and alkane line 80 feed directly into flooded gas mixer 240. A homogeneous mixture that includes hydrocarbon and oxygen, and optionally an inert diluent, can be introduced into ODH reactor 10 from flooded gas mixer 240 via mixed line 250 (FIG. 2). Oxygen enriched bottom line 220 may feed directly into or in combination with oxygen line 70 into flooded gas mixer 240.

The temperature of the contents within product line 90 in a typical ODH process can reach about 450° C. It can be desirable to lower the temperature of the stream before introduction into quench tower or acetic acid scrubber 20 as described above. In that instance, the present disclosure contemplates the use of a heat exchanger immediately downstream of each ODH reactor 10 and immediately upstream of quench tower 20. Use of a heat exchanger to lower temperatures in this fashion is well known in the art.

As indicated above, with reference to FIG. 1, in the ODH process configuration depicted in FIG. 2, although second reactor 25 is shown directly after quench tower or acetic acid scrubber 20, it can be placed further downstream. In many cases, the process configuration can be more energy efficient if second reactor 25 is placed after the input stream has been compressed.

In many embodiments of the disclosure, the olefins produced using the one or more ODH reactors, or any of the processes or complexes described herein, can be used to make various olefin derivatives. Olefin derivatives include, but are not limited to polyethylene, polypropylene, ethylene oxide, propylene oxide, polyethylene oxide, polypropylene oxide, vinyl acetate, vinyl chloride, acrylic esters (e.g. methyl methacrylate), thermoplastic elastomers, thermoplastic olefins and blends and combinations thereof.

In many embodiments of the disclosure, ethylene and optionally α-olefins are produced in the one or more ODH reactors, or any of the processes or complexes described herein, and are used to make polyethylene. The polyethylene made from the ethylene and optional α-olefins described herein can include homopolymers of ethylene, copolymers of ethylene and α-olefins, resulting in HDPE, MDPE, LDPE, LLDPE and VLDPE.

The polyethylene produced using the ethylene and optional α-olefins described herein can be produced using any suitable polymerization process and equipment. Suitable ethylene polymerization processes include, but are not limited to gas phase polyethylene processes, high pressure polyethylene processes, low pressure polyethylene processes, solution polyethylene processes, slurry polyethylene processes and suitable combinations of the above arranged either in parallel or in series.

The present disclosure also contemplates use of various tools commonly used for chemical reactors, including flowmeters, compressors, valves, and sensors for measuring parameters such as temperature, pressure and flow rates. It is expected that the person of ordinary skill in the art would include these components as deemed necessary for safe operation.

A first aspect of the present disclosure relates to a method of converting one or more alkanes to one or more alkenes. The method includes:

a. providing a first stream including one or more alkanes and oxygen to an oxidative dehydrogenation reactor;

b. converting at least a portion of the one or more alkanes to one or more alkenes in the oxidative dehydrogenation reactor to provide a second stream exiting the oxidative dehydrogenation reactor including one or more alkanes, one or more alkenes, oxygen, one or both of carbon dioxide and carbon monoxide and optionally acetylene;

c. providing the second stream to a second reactor containing a catalyst including a group 11 metal and optionally a promoter including $CeO_2$, $ZrO_2$ and combinations thereof supported on $SiO_2$ to convert a least a portion of the carbon monoxide to carbon dioxide and reacting any acetylene.

In a second aspect, in the method according to the first aspect, the one or more alkanes include ethane.

In a third aspect, in the methods according to either of the first or second aspects, the one or more alkenes include ethylene.

In a fourth aspect, in the methods according to the first three aspects, the oxidative dehydrogenation reactor contains an oxidative dehydrogenation catalyst that includes one or more mixed metal oxides selected from:

i) Catalysts of the Formula:

$Mo_aV_bTe_cNb_dPd_eO_f$ wherein a, b, c, d, e and f are the relative atomic amounts of the elements Mo, V, Te, Nb, Pd and O, respectively; and when a=1, b=0.01 to 1.0, c=0.01 to 1.0, d=0.01 to 1.0, 0.00≤e≤0.10 and f is a number to satisfy the valence state of the catalyst;

ii) Catalysts of the Formula:

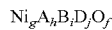
$Ni_gA_hB_iD_jO_f$ wherein: g is a number from 0.1 to 0.9, in some cases from 0.3 to 0.9, in other cases from 0.5 to 0.85, in some instances 0.6 to 0.8; h is a number from 0.04 to 0.9; i is a number from 0 to 0.5; j is a number from 0 to 0.5; and f is a number to satisfy the valence state of the catalyst; A is chosen from Ti, Ta, V, Nb, Hf, W, Y, Zn, Zr, Si and Al or mixtures thereof; B is chosen from La, Ce, Pr, Nd, Sm, Sb, Sn, Bi, Pb, Tl, In, Te, Cr, Mn, Mo, Fe, Co, Cu, Ru, Rh, Pd, Pt, Ag, Cd, Os, Ir, Au, Hg, and mixtures thereof; D is chosen from Ca, K, Mg, Li, Na, Sr, Ba, Cs, and Rb and mixtures thereof; and O is oxygen;

iii) Catalysts of the Formula:

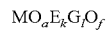
$Mo_aE_kG_lO_f$ wherein: E is chosen from Ba, Ca, Cr, Mn, Nb, Ta, Ti, Te, V, W and mixtures thereof; G is chosen from Bi, Ce, Co, Cu, Fe, K, Mg, V, Ni, P, Pb, Sb, Si, Sn, Ti, U, and mixtures thereof; a=1; k is 0 to 2; l=0 to 2, with the proviso that the total value of I for Co, Ni, Fe and mixtures thereof is less than 0.5; and f is a number to satisfy the valence state of the catalyst;

iv) Catalysts of the Formula:
$V_mMo_nNb_oTe_pMe_qO_f$
wherein: Me is a metal chosen from Ta, Ti, W, Hf, Zr, Sb and mixtures thereof; m is from 0.1 to 3; n is from 0.5 to 1.5; o is from 0.001 to 3; p is from 0.001 to 5; q is from 0 to 2; and f is a number to satisfy the valence state of the catalyst;

v) Catalysts of the Formula:

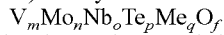
$Mo_aV_rX_sY_tZ_uM_vO_f$ wherein: X is at least one of Nb and Ta; Y is at least one of Sb and Ni; Z is at least one of Te, Ga, Pd, W, Bi and Al; M is at least one of Fe, Co, Cu, Cr, Ti, Ce, Zr, Mn, Pb, Mg, Sn, Pt, Si, La, K, Ag and In; a=1.0 (normalized); r=0.05 to 1.0; s=0.001 to 1.0; t=0.001 to 1.0; u=0.001 to 0.5; v=0.001 to 0.3; and f is a number to satisfy the valence state of the catalyst;

vi) A Mixed Metal Oxide Having the Empirical Formula:

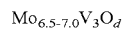
$Mo_{6.5-7.0}V_3O_d$ where d is a number to satisfy the valence of the oxide; and vii) A Mixed Metal Oxide Having the Empirical Formula:

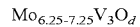
$Mo_{6.25-7.25}V_3O_d$ where d is a number to satisfy the valence of the oxide.

In a fifth aspect, in the methods according to the first four aspects, the first stream can include one or more inert diluents, an oxygen containing gas and a gas containing one or more lower alkanes.

In a sixth aspect, in the methods according to the first five aspects, the second stream can include one or more unreacted lower alkanes; one or more lower alkenes; oxygen; one or more inert diluents; carbon dioxide; carbon monoxide; acetic acid; and water.

In a seventh aspect, in the methods according to the first six aspects, the oxidative dehydrogenation reactor includes a single fixed bed type reactor.

In an eighth aspect, in the methods according to the first six aspects, the oxidative dehydrogenation reactor includes a single fluidized bed type reactor.

In a ninth aspect, in the methods according to the first six aspects, the oxidative dehydrogenation reactor includes a swing bed type reactor arrangement and/or a moving bed reactor.

In a tenth aspect, in the methods according to the first nine aspects, the group 11 metal is selected from the group of copper, silver, gold and combinations thereof.

In an eleventh aspect, in the methods according to the first ten aspects, the group 11 metal is silver or copper.

In a twelfth aspect, in the methods according to the first eleven aspects, the catalyst in the second reactor includes Ag/SiO$_2$, AgCeO$_2$/SiO$_2$, AgZrO$_2$/SiO$_2$, Cu/SiO$_2$, CuCeO$_2$/SiO$_2$, CuZrO$_2$/SiO$_2$, CuCo$_3$O$_4$/SiO$_2$ and combinations thereof.

In a thirteenth aspect, in the methods according to the first twelve aspects, an acetic acid scrubber is placed between the oxidative dehydrogenation reactor and the second reactor.

In a fourteenth aspect, in the methods according to the first thirteen aspects, the temperature in the second reactor is from 40 to 100° C.

A fifteenth aspect of the disclosure is directed to a chemical complex for oxidative dehydrogenation of lower alkanes, the chemical complex includes in cooperative arrangement:

i) at least one oxidative dehydrogenation reactor, that includes an oxidative dehydrogenation catalyst designed to accept, optionally in the presence of an inert diluent, an oxygen containing gas and a lower alkane containing gas, and to produce a product stream that includes the corresponding alkene and possibly one or more of:
  a. unreacted lower alkane;
  b. oxygen;
  c. inert diluent;
  d. carbon oxides, including carbon dioxide and carbon monoxide;
  e. oxygenates, including acetic acid, acrylic acid, maleic anhydride and maleic acid; and
  f. water;

ii) a quench tower for quenching the product stream and for removing water and soluble oxygenates from said product stream;

iii) an oxidation reactor for oxidizing carbon monoxide to carbon dioxide and optionally reacting acetylene;

iv) an amine wash for removing carbon dioxide from said product stream;

v) a dryer for removal of water from said product stream;

vi) a distillation tower for removing C2/C2+ hydrocarbons from said product stream to produce an overhead stream enriched with C1 hydrocarbons;

vii) optionally, a means for introducing a combustible fuel into said overhead stream; and viii) an oxygen separation module that includes:
  a. an oxygen transport membrane housed inside a sealed vessel and having a retentate side and a permeate side;
  b. a first inlet for introducing said overhead stream, combustible fuel, or both into said retentate side;
  c. a second inlet for introducing said overhead stream, combustible fuel, or both into said permeate side;
  d. an air inlet for introducing air into the retentate side;
  e. an exhaust for discharge of oxygen depleted air and combustion products from said retentate side; and
  f. an outlet for removing oxygen enriched gas and combustion products from said permeate side;

where the components in i) through viii) are connected in series in the sequence described, the overhead stream from vi) may be directed into said retentate side, the permeate side, or both the retentate side and the permeate side, and the oxygen enriched gas and combustion products from the permeate side may be directed back to i) as or part of the oxygen containing gas introduced into the at least one oxidative dehydrogenation reactor.

A sixteenth aspect of the disclosure is directed to a chemical complex according to the chemical complex of aspect 15 that includes a non-flammable liquid flooded gas mixer for premixing the oxygen containing gas, the lower alkane containing gas and inert gases prior to introduction into the at least one oxidative dehydrogenation reactor. In many aspects, when the non-flammable liquid inside the complex is water, then the generated saturated steam in the overhead of the mixer can also act as an inert diluent (in addition to the fed inert gases).

A seventeenth aspect of the disclosure is directed to a chemical complex according to the fifteenth and sixteenth aspects, where the oxidative dehydrogenation catalyst includes one or more of the mixed metal oxides described in the fourth aspect above.

An eighteenth aspect is directed to a chemical complex according to any of aspects 15 through 17, where the at least one oxidative dehydrogenation reactor includes a single fixed bed type reactor.

A nineteenth aspect is directed to a chemical complex according to any of aspects 15 through 17, where the at least one oxidative dehydrogenation reactor includes a single fluidized bed type reactor.

A twentieth aspect is directed to a chemical complex according to any of aspects 15 through 17, where the at least one oxidative dehydrogenation reactor includes a swing bed type reactor arrangement.

A twenty-first aspect is directed to a chemical complex according to any of aspects 15 through 20, where the at least one oxidative dehydrogenation reactor includes more than one oxidative dehydrogenation reactor, each including the same or different oxidative dehydrogenation catalyst, connected in series, and where the product stream from each oxidative dehydrogenation reactor except the last oxidative dehydrogenation reactor in the series is fed into a downstream oxidative dehydrogenation reactor.

A twenty-second aspect is directed to a chemical complex according to any of aspects 15 through 20, where the at least one oxidative dehydrogenation reactor includes more than one oxidative dehydrogenation reactor connected in parallel and each includes the same or different oxidative dehydrogenation catalyst.

A twenty-third aspect is directed to a chemical complex according to any of aspects 15 through 22, where the chemical complex includes at least one heat exchanger immediately upstream of the quench tower.

A twenty-fourth aspect is directed to a chemical complex according to any of aspects 15 through 23, where the chemical complex includes a caustic wash tower immediately downstream of the amine wash.

A twenty-fifth aspect is directed to a chemical complex according to any of aspects 15 through 24, where the C2/C2+ hydrocarbons leave the distillation tower and are directed to a splitter for separation of unreacted lower alkane and corresponding alkene into an unreacted lower alkane stream and a corresponding alkene stream.

A twenty-sixth aspect is directed to a chemical complex according to any of aspects 15 through 25, where the distillation tower further provides for separation of the C2/C2+ hydrocarbons portion of the product stream into an unreacted lower alkane stream and a corresponding alkene stream.

A twenty-seventh aspect is directed to a chemical complex according to any of aspects 15 through 26, where the unreacted lower alkane stream is directed back to the at least one oxidative dehydrogenation reactor as part of the lower alkane containing gas.

A twenty-eighth aspect is directed to a chemical complex according to any of aspects 15 through 27, where the oxygen separation module is tubular and the oxygen transport membrane includes an inner tube that is within an outer shell and where the retentate side includes the annular space between the inner tube and outer shell and the permeate side is the space within the inner tube.

A twenty-ninth aspect is directed to a chemical complex according to any of aspects 15 through 28, where the oxygen separation module includes an additional inlet into the retentate side, the permeate side, or both, for introduction of combustible fuel into the oxygen separation module.

A thirtieth aspect is directed to a chemical complex according to any of aspects 15 through 29, where the oxidation reactor contains a catalyst that includes a group 11 metal.

A thirty-first aspect is directed to a chemical complex according to any of aspects 15 through 30, where the oxidation reactor contains a catalyst that includes a group 11 metal selected from copper, silver, gold and combinations thereof.

A thirty-second aspect is directed to a chemical complex according to any of aspects 15 through 31, where the oxidation reactor contains a catalyst that includes silver or copper.

A thirty-third aspect is directed to a chemical complex according to any of aspects 15 through 32, where the oxidation reactor contains a catalyst that contains a catalyst that includes $Ag/SiO_2$, $AgCeO_2/SiO_2$, $AgZrO_2/SiO_2$, $Cu/SiO_2$, $CuCeO_2/SiO_2$, $CuZrO_2/SiO_2$, $CuCo_3O_4/SiO_2$ and combinations thereof.

A thirty-fourth aspect is directed to a chemical complex according to any of aspects 15 through 33, where the stream entering the oxidation reactor includes from 100 ppm to 5 wt. % oxygen and optionally from 1 vppm to 1000 vppm acetylene.

A thirty-fifth aspect is directed to a chemical complex according to any of aspects 15 through 34, where the stream exiting the oxidation reactor is essentially free of oxygen and acetylene.

A thirty-sixth aspect is directed to a chemical complex according to any of aspects 15 through 35, where the amount of carbon dioxide in the stream entering the oxidation reactor is greater than the amount of carbon dioxide in the stream exiting the oxidation reactor.

A thirty-seventh aspect is directed to a chemical complex according to any of aspects 15 through 36, where the amount of carbon monoxide in the stream entering the oxidation reactor is less than the amount of carbon monoxide in the stream exiting the oxidation reactor.

A thirty-eighth aspect is directed to a chemical complex according to any of aspects 15 through 37, where the temperature in the oxidation reactor is from about 40 to about 100° C.

A thirty-ninth aspect is directed to method of converting one or more alkanes to one or more alkenes in a carbon dioxide negative process that includes (a) providing a first stream containing one or more alkanes, steam, carbon dioxide and oxygen to an oxidative dehydrogenation reactor; (b) converting at least a portion of the one or more alkanes to one or more alkenes in the oxidative dehydrogenation reactor to provide a second stream exiting the oxidative dehydrogenation reactor containing one or more alkanes, one or more alkenes, carbon dioxide and one or more of oxygen and carbon monoxide; where the total amount of carbon dioxide in the second stream is less than the total amount of carbon dioxide in the first stream.

A fortieth aspect is directed to method of converting one or more alkanes to one or more alkenes that includes (a) providing a first stream containing one or more alkanes and oxygen to an oxidative dehydrogenation reactor; and (b) converting at least a portion of the one or more alkanes to one or more alkenes in the oxidative dehydrogenation reactor to provide a second stream exiting the oxidative dehydrogenation reactor containing one or more alkanes, one or more alkenes and one or more of oxygen, carbon monoxide and carbon dioxide; where the volumetric ratio of oxygen to one or more alkanes in the first stream is from 0.3 to 1 and where the product selectivity for carbon dioxide is less than 10 weight percent.

A forty-first aspect is directed to a method of converting one or more alkanes to one or more alkenes that includes (a) providing a first stream containing one or more alkanes, steam, carbon dioxide and oxygen to an oxidative dehydrogenation reactor; and (b) converting at least a portion of the one or more alkanes to one or more alkenes in the oxidative dehydrogenation reactor to provide a second stream exiting the oxidative dehydrogenation reactor containing one or more alkanes, one or more alkenes, carbon dioxide and one or more of oxygen and carbon monoxide; where the amount of carbon dioxide in the second stream is ±10 weight percent of the amount of carbon dioxide in the first stream.

A forty-second aspect is directed to a method of converting one or more alkanes to one or more alkenes that includes (a) providing a first stream containing one or more alkanes and oxygen to an oxidative dehydrogenation reactor; and (b) converting at least a portion of the one or more alkanes to one or more alkenes in the oxidative dehydrogenation reactor to provide a second stream exiting the oxidative dehydrogenation reactor contains one or more alkanes and one or more alkenes; where the amount of carbon dioxide in the second stream is equal to the amount of carbon dioxide in the first stream.

A forty-third aspect is directed to any of aspects 1 through 41, where carbon dioxide is recycled to at least one oxidative dehydrogenation reactor.

A forty-fourth aspect is directed to any of aspects 1 through 42, where the olefins produced using the one or more ODH reactors, or any of the processes or complexes described herein, can be used to make olefin derivatives.

A forty-fifth aspect is directed to aspect 43, where the olefin derivatives include, but are not limited to polyethylene, polypropylene, ethylene oxide, propylene oxide, polyethylene oxide, polypropylene oxide, thermoplastic elastomers, thermoplastic olefins and blends and combinations thereof.

A forty-sixth aspect is directed to any of aspects 1 through 42, where the ethylene and optional α-olefins produced in the one or more ODH reactors, or any of the processes or complexes described herein, is used to make polyethylene.

A forty-seventh aspect is directed to aspect 45, where the polyethylene includes one or more of homopolymers of ethylene, copolymers of ethylene and α-olefins, HDPE, MDPE, LDPE, LLDPE, VLDPE and combinations and blends thereof.

A forty-eighth aspect is directed to aspect 45, where the polyethylene is produced using one or more processes including gas phase polyethylene processes, high pressure polyethylene processes, low pressure polyethylene processes, solution polyethylene processes, slurry polyethylene processes and suitable combinations of the above arranged either in parallel or in series.

The following examples are intended to aid in understanding the present disclosure, however, in no way, should these examples be interpreted as limiting the scope thereof.

EXAMPLES

Example 1

The effect of altering the amount of steam injected into an ODH process on the carbon dioxide output was demonstrated using two fixed bed reactors, connected in series. The catalyst present in each of the reactors was a mixture of several batches of a mixed metal oxide catalyst of the formula: $Mo_{1.0}V_{0.30-0.50}Te_{0.10-0.20}Nb_{0.10-0.20}O_d$, where the subscripts represent the range of atomic amounts of each element, relative to Mo, present in the individual batches, and d represents the highest oxidation state of the metal oxides present in the catalyst. Ethane, carbon dioxide, and oxygen were premixed before addition of water, followed by preheating with the entire composition being fed to the first of the two reactors. The preheating step was necessary to ensure the water added was converted to steam before injection into the reactor. Output from the first reactor was sent directly into the second reactor without addition of new reactants. For each reactor, the temperature was held in the range of 334-338° C. at ambient pressure. The process was run continuously over a period of three days.

The relative amounts of ethane, carbon dioxide, and oxygen remained the same while the flow rate of steam added to reactor was altered. The relative amounts of ethane, carbon dioxide, and oxygen added to the first reactor were 33, 54, and 13 respectively. The gas hourly space velocity (GHSV) was kept constant at 610 h$^{-1}$. Flow rates of reaction ethane, carbon dioxide and oxygen were altered accordingly to maintain GHSV at 610 h$^{-1}$ after altering the amount of steam added to reactor.

Steam was added indirectly as water with the ethane, carbon dioxide and oxygen mixture. The amount of water added to the mixture before entering the first reactor was varied, starting with no water and increasing in increments up to a flow rate of 1.0 cm$^3$/min. For each flow rate of water added to the mixture, a corresponding weight % of steam in the total feed mixture was calculated. Table 1 shows the effect that changing the amount of steam added to the reactor had on output of carbon dioxide, carbon monoxide, and acetic acid. The output of the components was measured as normalized selectivity, according to the formula:

$$X \text{ selectivity (Wt \%)} = \frac{\text{net mass flow rate} \times (g\,x/hr)}{\frac{\text{mass flow rate } C_2H_6 (g\,C_2H_6/min)}{C_2H_6 \text{ molecular weight } (g\,C_2H_6/\text{mol } C_2H_6)} \times X \text{ molecular weight} \left(g\frac{X}{\text{mol } X}\right) \times \frac{N \text{ mol equivalent of compound } X}{1 \text{ mol } C_2H_6}}$$

where X refers to one of ethylene, $CO_2$, CO, and acetic acid.

Results listed in Table 1 were averaged from two or more experimental runs at each of the prescribed conditions. The results demonstrate that increasing the flow rate of water added to the mixture and corresponding increase in the weight % of steam added to the reactor led to a decrease in the carbon selectivity. A carbon dioxide negative process was seen when the water was added at a flow rate of 1.0 cm$^3$/min, which corresponds to 39 weight % of steam added. Also, reverting back to no steam added followed by increasing to 39 weight % resulted in the carbon dioxide selectivity going positive back to negative. Finally, it should be noted that increasing the steam resulted in a higher production of acetic acid and also was accompanied by a higher conversion rate of ethane.

TABLE 1

Normalized Selectivity of ODH Products in Response to Changes in Steam Added to the Reactor

| Experiment Number | Water (not Steam) Added (cm$^3$/min) | Steam Added (wt. %) | Ethane Conversion (%) | Selectivity (wt. %) | | | |
|---|---|---|---|---|---|---|---|
| | | | | Ethylene | CO$_2$ | CO | Acetic Acid |
| 1-1 | 0.0 | 0 | 38.4 | 83.0 | 6.30 | 8.1 | 2.6 |
| 1-2 | 0.1 | 3 | 41.6 | 82.0 | 6.0 | 7.7 | 4.3 |
| 1-3 | 0.4 | 13 | 43.5 | 79.2 | 6.0 | 7.0 | 7.7 |
| 1-4 | 0.8 | 29 | 45.8 | 79.2 | 3.6 | 6.8 | 10.4 |
| 1-5 | 1.0 | 39 | 49.8 | 88.7 | −9.8 | 7.3 | 13.8 |
| 1-6 | 0.0 | 0 | 37.9 | 84.2 | 4.4 | 7.8 | 3.7 |
| 1-7 | 1.0 | 39 | 50.0 | 90.4 | −10.5 | 7.3 | 12.8 |

Example 2

For each of experiment numbers 1-1 through 1-7 in Table 1, acetic acid/water is removed from the ODH product stream. The remaining stream is fed to a reactor containing an AgCeO$_2$/SiO$_2$ catalyst (particle size less than 5 nm), prepared by impregnating silica with an aqueous silver nitrate solution, at from 105 to 115° C. The CO in the stream is reacted with oxygen in the stream to form CO$_2$. The stream exiting the reactor contains less CO and O2 and more CO$_2$ than the stream entering the reactor.

Example 3

For each of experiment numbers 1-1 through 1-7 in Table 1, acetic acid is removed from the ODH product stream. The remaining stream is fed to a reactor containing AgZrO$_2$/SiO$_2$ catalyst (particle size less than 5 nm), prepared by impregnating silica with an aqueous silver nitrate solution, at from 105 to 115° C. The CO in the stream is reacted with oxygen in the stream to form CO$_2$. The stream exiting the reactor contains less CO and O2 and more CO$_2$ than the stream entering the reactor.

Example 4

A second experiment was conducted using the same reactor configuration from Example 1 but under different operating conditions. The catalyst included a mix of several batches as described for Example 1, and for comparison included a freshly mixed catalyst (fresh) and a mixed catalyst 8 months after being used intermittently used. The relative volumetric amounts of ethane, carbon dioxide, and oxygen added to the first reactor were 42, 37, and 21 respectively. Note the higher volumetric feed ratio of $O_2/C_2H_6$ used compared to Example 1. Also, the gas hourly space velocity (GHSV) was higher, and kept constant at 1015 h$^{-1}$, with reaction temperature being held from between 321 to 325° C. Similar to Example 1, flow rates of ethane, carbon dioxide and oxygen were altered accordingly to maintain GHSV at 1015 h$^{-1}$ after altering the amount of water added. The corresponding steam content added to the first reactor was changed from 0 wt. % to 16 wt. %.

The results of this experiment, shown in Table 2, demonstrated that when compared to the fresh catalyst (experiment 1) the used catalyst (experiment 4) displayed an increased selectivity towards the production of by-products, most notably $CO_2$, with a concomitant decrease in ethylene selectivity. The fresh catalyst showed 91% selectivity to $C_2H_6$ and a negative $CO_2$ selectivity of −1.0. With the used catalyst selectivity to $C_2H_6$ dropped to 89% and $CO_2$ selectivity moved into positive territory at 5.0. Experiment 3 with the used catalyst demonstrated that the disclosed methods are also effective with a used catalyst, as increasing weight % of steam added to reactor from 0 to 16 weight % resulted in a drop in $CO_2$ selectivity to 3.0 from 5.0. This decrease was in good agreement with the observed trend in Example 1.

TABLE 2

Normalized Selectivity of ODH Products using Higher Feed Ratio of $O_2/C_2H_6$ and with Fresh Versus Used Catalyst

| Experiment Number | Water (not Steam) Added (cm³/min) | Steam Added (wt. %) | Ethane Conversion (%) | Selectivity (wt. %) | | | |
|---|---|---|---|---|---|---|---|
| | | | | Ethylene | $CO_2$ | CO | Acetic Acid |
| 4-1 (fresh) | 0.0 | 0 | 31.0 | 91.0 | −1.0 | 5.0 | 5.0 |
| 4-2 (used) | 0.0 | 0 | 26.0 | 89.0 | 5.0 | 4.0 | 3.0 |
| 4-3 (used) | 0.97 | 16 | 35.0 | 87.0 | 3.0 | 4.0 | 5.0 |

Example 5

For each of experiment numbers 1 through 3 in Table 2, acetic acid is removed from the ODH product stream. The remaining stream is fed to a reactor containing an $AgZrO_2/SiO_2$ catalyst (particle size less than 5 nm), prepared by impregnating silica with an aqueous silver nitrate solution, at from 105 to 115° C. The CO in the stream is reacted with oxygen in the stream to form $CO_2$.
The stream exiting the reactor contains less CO and O2 and more $CO_2$ than the stream entering the reactor.

Example 6

For each of experiment numbers 1 through 3 in Table 2, acetic acid is removed from the ODH product stream. The remaining stream is fed to a reactor containing an $AgCeO_2/SiO_2$ catalyst (particle size less than 5 nm), prepared by impregnating silica with an aqueous silver nitrate solution, at from 105 to 115° C. The CO in the stream is reacted with oxygen in the stream to form $CO_2$. The stream exiting the reactor contains less CO and O2 and more $CO_2$ than the stream entering the reactor.

Examples 7-11 (CO Selective Oxidation Process)

Experimental Reactor Unit (ERU) Setup

Figure 4:
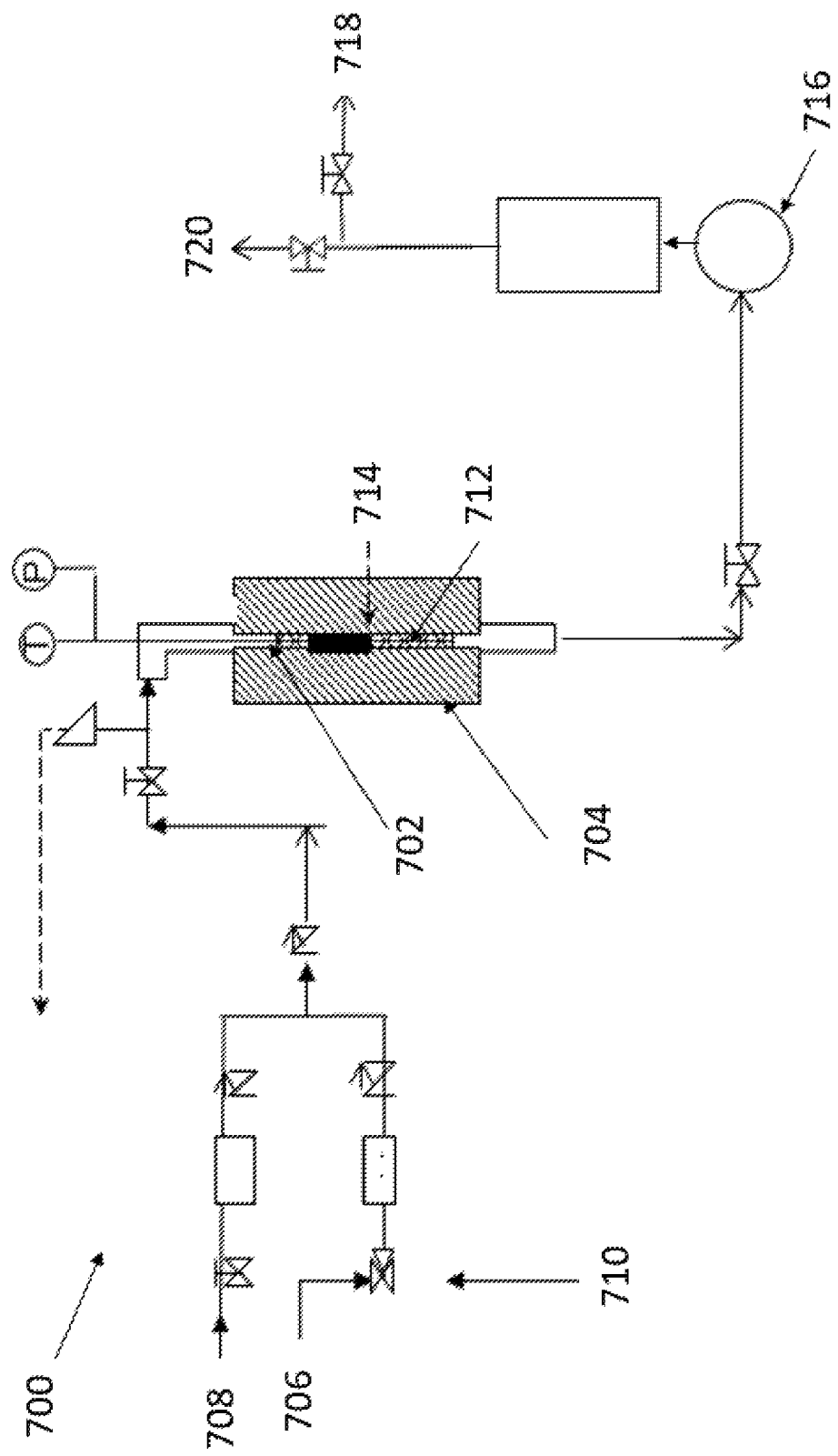
FIG. 4—Schematic of the experimental reactor unit as described in the examples.

The ERU was used to produce feed gas for evaluating catalysts according to the disclosure. The apparatus (700 in FIG. 4) consists of fixed bed tube reactor 702, which is surrounded by two-zone electric heater 704. Reactor 702 is a 316L stainless steel tube which has an outside diameter of 0.5 inches (about 1.27 cm) and inside diameter of 0.4 inches (about 1 cm) and a length of 14.96 inches (about 38 cm). Two main feed gas lines are attached to reactor 702; one line 706 is dedicated for a bulk nitrogen purge gas and the other line 708 is connected to a dual solenoid valve, which can be switched from ODH process feed gas (gas mixture of ethane/oxygen/Nitrogen at a molar ratio of about 36/18/46) to compressed air when regenerating catalyst bed 714.

For safety reasons the unit is programmed in a way that prevents air from mixing with the feed gas. This is accomplished through safety interlocks and a mandatory 15-minute nitrogen purge of the reactor when switching between feed gas 706 and air 710. The flow of gases is controlled by mass flow controllers. A 6-point thermocouple 712 is inserted through reactor 702, which is used to measure and control the temperature within catalyst bed 714. The catalyst is loaded in the middle zone of reactor 702 and located in between points 3 and 4 of thermocouple 712, which are the reaction temperature control points. The remaining 4 points of thermocouple 712 are used for monitoring purposes.

Catalyst bed 714 consists of a one to one volume ratio of catalyst to quartz sand, a total of 3 ml. The rest of reactor 702, below and above catalyst bed 714 is packed with 100% quartz sand and the load is secured with glass wool on the top and the bottom of reactor 702. A glass tight sealed condenser 716 is located after reactor 702 at room temperature to collect water/acidic acid and the gas product can flow to either vent 720 or sampling loop/vent 718 by a three-way solenoid valve.

CO Selective Oxidation Catalyst Testing Reactor

A 316L stainless steel tube with the following dimensions was used to test CO selective oxidation catalysts:

Outside diameter: 0.25 inches (about 0.63 cm)

Wall thickness: 0.028 inches (about 0.07 cm)

Catalyst bed height: 2 inches (about 5 cm)

The total weight of the catalyst is recorded for each catalyst, which was tested. The flow of gases is controlled by the mass flow controllers on the ERU. The product gas from the ERU is directly fed in to the CO selective oxidation catalyst testing reactor ("Testing Rector"). The Testing Reactor was placed in a precision heating oven, in which the temperature was controlled within less than 0.5° C. There were no thermocouples inside the reactor catalyst bed itself, as a result, the oven temperature was recorded as the catalyst testing temperature. The catalyst bed consisted of approximately 1 g of catalyst supported between two layers of glass quartz wool. The effluent from the reactor was continuously provided for gas chromatography analysis.

AgCe on Silica Catalyst Sample

SYLOPOL® 2408 silica (W. R. Grace, surface area: 316 m²/g, pore volume: 1.54 cc/g, 20 g) was impregnated with a solution (40 ml) of $Ce(NO_3)_3 \cdot 6H_2O$ (2.80 g) and X. The impregnated silica was dried at 90° C. overnight and was calcined in air at 500° C. for 6 hours.

X=$AgNO_3$, 103 mL of 0.1N solution. The solution was concentrated to about 20 ml and mixed with $Ce(NO_3)_3 \cdot 6H_2O$. Distilled water was added to make 40 ml.

The catalyst made was CeAg oxide on silica with $CeO_2$: 5 wt %, Ag: 5 wt %.

CuCe on Silica Catalyst Sample

SYLOPOL 2408 silica (20 g) was impregnated with a solution (40 ml) of $Ce(NO_3)_3 \cdot 6H_2O$ (2.80 g) and Y. The impregnated silica was dried at 90° C. overnight and was calcined in air at 500° C. for 6 hours.

Y=$Cu(CH_3COO)_2$, 3.17 g. The solution was concentrated to about 20 ml and was mixed with $Ce(NO_3)_3 \cdot 6H_2O$. Distilled water was added to make 40 ml. The catalyst made was CeCu oxide on silica with $CeO_2$: 5 wt %, Cu: 5 wt %.

MnCe on Silica Catalyst Sample

SYLOPOL 2408 silica (20 g) was impregnated with a solution (40 ml) of $Ce(NO_3)_3 \cdot 6H_2O$ (2.80 g) and Z. The impregnated silica was dried at 90° C. overnight and was calcined in air at 500° C. for 6 hours.

Z=$MnCl_2 \cdot 4H_2O$, 4.0 g. The solution was concentrated to about 20 ml and was mixed with $Ce(NO_3)_3 \cdot 6H_2O$. Distilled water was added to make 40 ml. The catalyst made was CeMn oxide on silica with $CeO_2$: 5 wt %, Mn: 5 wt %.

CrCe on Silica Catalyst Sample

SYLOPOL 2408 silica (20 g) was impregnated with a solution (40 ml) of $Ce(NO_3)_3 \cdot 6H_2O$ (2.80 g) and W. The impregnated silica was dried at 90° C. overnight and was calcined in air at 500° C. for 6 hours.

W=$Cr(NO_3)_3 \cdot 9H_2O$, 6.98 g. The solution was concentrated to about 20 ml and was mixed with $Ce(NO_3)_3 \cdot 6H_2O$. Distilled water was added to make 40 ml. The catalyst made was CeCr oxide on silica with $CeO_2$: 5 wt %, Cr: 5 wt %.

Example 7

AgCe on Silica Catalyst Testing

The ODH process was run using the ERU and catalyst MoVOx to provide the feed for this example. 0.15 g of AgCe catalyst was used for this test at a gas hourly space velocity of approximately 5000 h-1, 0 psig on the reactor outlet, at 75° C. process temperature. The results are shown in the table below.

|  | $C_2H_6$ Vol. % | $C_2H_4$ Vol. % | $O_2$ Vol. % | $N_2$ Vol. % | $CO_2$ Vol. % | CO Vol. % | $C_2H_2$ vppm |
|---|---|---|---|---|---|---|---|
| Feed | 20.59 | 15.84 | 0.48 | 55.09 | 2.32 | 5.67 | 220 |
| Product | 21.44 | 16.53 | 0.06 | 54.06 | 3.37 | 4.50 | <1 |

The data show that the AgCe catalyst demonstrates excellent oxygen removal properties via selective oxidation of CO to $CO_2$, which can be seen from noticeable reduction of CO in the product gas and increase in all of the other compounds. It is noteworthy that acetylene is also fully oxidized and was not detected in the product gas from the Testing Reactor.

Example 8

1.7 g of AgCe catalyst was used for this test, with approximately 1 g of the catalyst present in the hot zone of the reactor. 1 g was the value for the catalyst weight used for the long term test calculations. In this example, the ODH catalyst used to produce the feed for this example was a MoVOx catalyst (same as example 7). In this example, the feed sample to the selective CO oxidation reactor was taken at the beginning and at the end of the test in order to confirm the composition of the feed. The test was executed at 110° C. process temperature, 0 psig reactor outlet pressure, gas hourly space velocity of approximately 3000 h$^{-1}$. The results are summarized in the table below.

|  | Time on Stream H | $C_2H_6$ Vol. % | $C_2H_4$ Vol. % | $O_2$ Vol. % | $CO_2$ Vol. % | $N_2$ Vol. % | CO Vol. % | $C_2H_2$ vppm | $O_2$ Removed % |
|---|---|---|---|---|---|---|---|---|---|
| Feed-Beginning | 0 | 23.283 | 12.448 | 0.539 | 2.820 | 55.747 | 5.163 | 67 |  |
| Product | 3 | 23.237 | 12.529 | 0.222 | 2.880 | 55.957 | 5.176 | <1 | 58.860 |
|  | 27 | 24.138 | 13.005 | 0.388 | 2.804 | 54.692 | 4.974 | <1 |  |
|  | 39 | 23.440 | 12.633 | 0.297 | 2.824 | 55.725 | 5.082 | <1 |  |
|  | 43 | 23.841 | 12.810 | 0.416 | 2.788 | 55.132 | 5.013 | <1 |  |
|  | 47 | 23.916 | 12.818 | 0.513 | 2.773 | 54.995 | 4.985 | <1 |  |
|  | 54 | 23.436 | 12.543 | 0.560 | 2.792 | 55.651 | 5.019 | <1 |  |
|  | 65 | 23.233 | 12.434 | 0.434 | 2.824 | 55.997 | 5.079 | <1 |  |
|  | 69 | 23.911 | 12.767 | 0.531 | 2.771 | 55.041 | 4.979 | <1 |  |
|  | 73 | 23.823 | 12.704 | 0.645 | 2.765 | 55.097 | 4.967 | <1 |  |
|  | 76 | 24.174 | 12.838 | 0.726 | 2.727 | 54.640 | 4.896 | <1 |  |
|  | 80 | 23.236 | 12.328 | 0.760 | 2.784 | 55.888 | 5.004 | <1 |  |
|  | 91 | 23.355 | 12.404 | 0.547 | 2.803 | 55.849 | 5.042 | <1 |  |
|  | 95 | 24.354 | 12.898 | 0.696 | 2.723 | 54.436 | 4.893 | <1 | 41.245 |
| Feed-End | 96 | 23.693 | 12.579 | 1.185 | 2.596 | 53.892 | 6.056 | 70 |  |

"$O_2$ removed" value is calculated as follows:

$$V_{O2} = \frac{(C_{O2feed} - C_{O2product}) * 100\%}{C_{O2\,feed}}$$

Where:
$V_{O2}$—the value of "$O_2$ removed"
C—volumetric concentration of oxygen in the feed and product gasses Because the composition of the feed to the selective CO oxidation reactor was changing gradually over the term of the experiment, accurate values for removed oxygen could only be calculated at the very beginning and at the very end of the run. The data show that even though the catalyst had very stable activity toward acetylene oxidation through the whole duration of the run, the activity toward $O_2$ removal via selective CO oxidation gradually decreased over the duration of the run. Generally, the amount of CO and $O_2$ in the product stream was less than in the feed stream and the amount of $CO_2$ in the product stream was greater than the amount in the feed stream.

|  | $C_2H_6$ Vol.-% | $C_2H_4$ Vol.-% | $O_2$ Vol.-% | $N_2$ Vol.-% | $CO_2$ Vol.-% | CO Vol.-% | $C_2H_2$ vppm |
|---|---|---|---|---|---|---|---|
| Feed | 22.318 | 12.963 | 0.176 | 56.020 | 2.643 | 5.879 | 90 |
| Product | 22.151 | 12.883 | 0.027 | 56.374 | 2.650 | 5.915 | <1 |

The data show that the AgCe catalyst was successfully regenerated. Acetylene was reduced to undetectable levels and oxygen levels in the product stream were less than in the feed stream.

Example 9

The ODH process of example 7 was used to provide the feed for this example. 0.35 g of AgCe catalyst, regenerated via oxidation, was used for this test. The test was executed at 110° C. process temperature, 0 psig reactor outlet pressure, gas hourly space velocity of approximately 3000 $h^{-1}$. The results are shown in the table below.

Example 10

The ODH process of example 7 was used to provide the feed for this example. 1.22 g of fresh CuCe catalyst was used for this test. The test was executed at 120° C. process temperature, 0 psig reactor outlet pressure, gas hourly space velocity of approximately 3000 $h^{-1}$. The results are summarized in the table below.

|  | $C_2H_6$ Vol.-% | $C_2H_4$ Vol.-% | $O_2$ Vol.-% | $N_2$ Vol.-% | $CO_2$ Vol.-% | CO Vol.-% | $C_2H_2$ vppm |
|---|---|---|---|---|---|---|---|
| Feed | 26.295 | 14.789 | 0.27915 | 51.35468 | 2.321394 | 4.960777 | 70 |
| Product | 25.268 | 14.453 | 0.024041 | 52.69556 | 2.532941 | 5.026455 | <1 |

The data show that the CuCe catalyst exhibits similar properties to the AgCe catalyst. CuCe catalyzes the reaction of selective oxidation of CO to $CO_2$ and oxidation of acetylene. However, this catalyst sample did not show any catalyst activity at a temperature of 110° C., which is noticeably higher than 75° C., at which fresh AgCe catalyst revealed significant activity toward selective oxidation of CO.

Example 11

The ODH process of example 7 was used to provide the feed for this example. 1.01 g of MnCe catalyst was used for this test. The test was executed at 140° C. process temperature, 0 psig reactor outlet temperature, gas hourly space velocity of approximately 3000 $h^{-1}$. The results are summarized in the table below.

|  | $C_2H_6$ Vol.-% | $C_2H_4$ Vol.-% | $O_2$ Vol.-% | $N_2$ Vol.-% | $CO_2$ Vol.-% | CO Vol.-% | $C_2H_2$ vppm |
|---|---|---|---|---|---|---|---|
| Feed | 25.711 | 14.124 | 0.7582 | 51.96842 | 2.346412 | 5.091964 | 90 |
| Product | 25.55 | 14.603 | 0.32696 | 52.10005 | 2.400248 | 5.019739 | 90 |

The data show that the MnCe catalyst exhibits selective CO oxidation properties, however, it did not demonstrate any activity toward oxidation of acetylene. This catalyst sample did not show any catalytic activity at the temperature below 140° C., which is noticeably higher than 75° C., at which AgCe catalyst revealed significant activity toward selective oxidation of CO.

Example 12

This experiment was conducted using the same reactor configuration as the previous example 4, but only using the second reactor in the series and under variable feed volume ratios of oxygen to ethane. The catalyst used was a mixed metal oxide catalyst of the formula: $Mo_{1.0}V_{0.37}Te_{0.23}Nb_{0.14}O_{4.97}$ and was extruded with ~55 wt. % of VERSAL™ 250 support (UOP LLC) in balance mixed metal oxide. Three relative volumetric amounts of oxygen and ethane were tested, including 16 vol % $O_2$: 38 vol % $C_2H_6$, 19 vol % $O_2$: 36 vol % $C_2H_6$, and 21 vol % $O_2$: 33 vol % $C_2H_6$, which correspond to $O_2$:$C_2H_6$ volumetric ratios of 0.4, 0.5, and 0.6, respectively. The relative volumetric amount of $CO_2$ added was maintained at 46 vol %, the gas hourly space velocity (GHSV) was kept constant at 1111 $h^{-1}$, the reaction temperature was held between 359° C. and 360° C., and reactions were performed at ambient pressure. No steam was added to the reaction.

The results of this example are shown in Table 3. As the volumetric ratio of oxygen:ethane is increased the selectivity towards the production of $CO_2$ decreases. This effect is accompanied by slight increases to selectivity towards ethylene and carbon monoxide, while acetic acid selectivity remains unchanged. Experiment 3 demonstrates that altering volumetric ratio of oxygen:ethane added to the reactor, while keeping other parameters unchanged, can decrease the selectivity to carbon dioxide. This effect is also demonstrated by comparing Examples 1 and 4, specifically experiment numbers 1-1 and 4-1 where no steam was added, in that the carbon selectivity was lower in experiment number 4-1 where a higher volumetric ratio of oxygen:ethane was added to the reactor.

TABLE 3

Normalized Product Selectivity of ODH Products in Response to Variations of Volumetric Feed Ratio of $O_2$/$C_2H_6$ at Elevated Temperature and Without the Addition of Steam Temp - 359-360° C.; GHSV - 1110 $h^{-1}$; Steam added - 0 vol %

| Experiment Number | Volumetric Feed Ratio $O_2$:$C_2H_6$ | Steam Added (wt. %) | Ethane Conversion (%) | Product Selectivity (wt. %) | | | |
|---|---|---|---|---|---|---|---|
| | | | | $C_2H_4$ | $CO_2$ | CO | $CH_3COOH$ |
| 12-1 | 0.4 | 0 | 48.0 | 83.5 | 7.0 | 6.4 | 3.1 |
| 12-2 | 0.5 | 0 | 49.0 | 84.1 | 6.0 | 7.1 | 2.9 |
| 12-3 | 0.6 | 0 | 47.0 | 86.4 | 2.1 | 8.2 | 3.3 |

Example 13

This experiment was conducted using the same reactor configuration as the previous examples and similar to example 1 but using a higher volumetric ratio of oxygen: ethane (0.5) added to the reactor, a higher GHSV (1111 $h^{-1}$), and a higher temperature of 360° C. The weight % of steam added to the reactor was changed from 0 wt. % to 40 wt. %, while keeping the relative volumetric amount of $CO_2$ steam added (46 vol %) constant. The results are presented in Table 4 and demonstrate that at higher temperatures, flow rates and volumetric ratio of oxygen:ethane increasing the amount of steam added to the reactor from 0 wt % to 40 wt % decreases the $CO_2$ selectivity. In this example, the $CO_2$ selectivity decreased from 6.0 wt. % to 5.3%. This decrease is lower than what is seen when operating at a lower temperature, low flow rate (GHSV), and lower relative volumetric ratio of oxygen:ethane added to the reactor.

TABLE 4

Normalized Product Selectivity of ODH Products in Response to Changes in Steam Added to the Reactor at Higher Temp., GHSV, and vol. ratio $O_2$:ethane Temp - 360° C.; GHSV - 1111 $h^{-1}$; Vol ratio $O_2$:$C_2H_6$ - 0.5

| Experiment Number | Steam Added (wt. %) | Ethane Conversion (wt. %) | Product Selectivity (wt. %) | | | |
|---|---|---|---|---|---|---|
| | | | $C_2H_4$ | $CO_2$ | CO | $CH_3COOH$ |
| 4-1 | 0 | 49 | 84.1 | 6.0 | 7.1 | 2.9 |
| 4-2 | 40 | 49 | 78.4 | 5.3 | 7.1 | 9.2 |

While the present disclosure has been particularly set forth in terms of specific embodiments thereof, it will be understood in view of the instant disclosure that numerous variations upon the disclosure are now enabled yet reside within the scope of the disclosure. Accordingly, the disclosure is to be broadly construed and limited only by the scope and spirit of the claims now appended hereto.

INDUSTRIAL APPLICABILITY

The present disclosure relates to converting alkanes to alkenes while mitigating the output of oxygen, carbon dioxide and/or acetylene from the process. When the alkane if ethane and the alkene is ethylene, the disclosure relates to producing homopolymers, copolymers, copolymer compositions and methods of making the same.

The invention claimed is:

1. A method of converting one or more alkanes to one or more alkenes comprising:
   a. providing a first stream comprising one or more alkanes and oxygen to an oxidative dehydrogenation reactor;
   b. converting at least a portion of the one or more alkanes to one or more alkenes in the oxidative dehydrogenation reactor to provide a second stream exiting the oxidative dehydrogenation reactor comprising one or more alkanes, one or more alkenes, acetylene and one or more of oxygen, carbon monoxide and carbon dioxide; and
   c. providing the second stream to a second reactor containing a catalyst comprising a group 11 metal and a promoter comprising $CeO_2$, $ZrO_2$ and combinations thereof supported on $SiO_2$ to react acetylene in the second stream.

2. The method according to claim 1, wherein the one or more alkanes comprise ethane.

3. The method according to claim 1, wherein the one or more alkenes comprise ethylene and optional α-olefins.

4. The method according to claim 1, wherein the oxidative dehydrogenation reactor contains an oxidative dehydrogenation catalyst comprising one or more mixed metal oxides chosen from:

i) catalysts of the formula:

$$Mo_a V_b Te_c Nb_d Pd_e O_f$$

wherein a, b, c, d, e and f are the relative atomic amounts of the elements Mo, V, Te, Nb, Pd and O, respectively; and when a=1, b=0.01 to 1.0, c=0.01 to 1.0, d=0.01 to 1.0, 0.00≤e≤0.10 and f is a number to satisfy the valence state of the catalyst;

ii) catalysts of the formula:

$$Ni_g A_h B_i D_j O_f$$

wherein: g is a number from 0.1 to 0.9; h is a number from 0.04 to 0.9; i is a number from 0 to 0.5; j is a number from 0 to 0.5; and f is a number to satisfy the valence state of the catalyst; A is chosen from Ti, Ta, V, Nb, Hf, W, Y, Zn, Zr, Si and Al or mixtures thereof; B is chosen from La, Ce, Pr, Nd, Sm, Sb, Sn, Bi, Pb, Tl, In, Te, Cr, Mn, Mo, Fe, Co, Cu, Ru, Rh, Pd, Pt, Ag, Cd, Os, Ir, Au, Hg, and mixtures thereof; D is chosen from Ca, K, Mg, Li, Na, Sr, Ba, Cs, and Rb and mixtures thereof; and O is oxygen;

iii) catalysts of the formula:

$$Mo_a E_k G_l O_f$$

wherein: E is chosen from Ba, Ca, Cr, Mn, Nb, Ta, Ti, Te, V, W and mixtures thereof; G is chosen from Bi, Ce, Co, Cu, Fe, K, Mg, V, Ni, P, Pb, Sb, Si, Sn, Ti, U, and mixtures thereof; a=1; k is 0 to 2; l=0 to 2, with the proviso that the total value of l for Co, Ni, Fe and mixtures thereof is less than 0.5; and f is a number to satisfy the valence state of the catalyst;

iv) catalysts of the formula:

$$V_m Mo_n Nb_o Te_p Me_q O_f$$

wherein: Me is chosen from Ta, Ti, W, Hf, Zr, Sb and mixtures thereof; m is from 0.1 to 3; n is from 0.5 to 1.5; o is from 0.001 to 3; p is from 0.001 to 5; q is from 0 to 2; and f is a number to satisfy the valence state of the catalyst;

v) catalysts of the formula:

$$Mo_a V_r X_s Y_t Z_u M_v O_f$$

wherein: X is at least one of Nb and Ta; Y is at least one of Sb and Ni; Z is at least one of Te, Ga, Pd, W, Bi and Al; M is at least one of Fe, Co, Cu, Cr, Ti, Ce, Zr, Mn, Pb, Mg, Sn, Pt, Si, La, K, Ag and In; a=1.0 (normalized); r=0.05 to 1.0; s=0.001 to 1.0; t=0.001 to 1.0; u=0.001 to 0.5; v=0.001 to 0.3; and f is a number to satisfy the valence state of the catalyst;

vi) a mixed metal oxide having the empirical formula:

$$Mo_{6.5-7.0}V_3 O_d$$

where d is a number to satisfy the valence of the oxide; and vii) a mixed metal oxide having the empirical formula:

$$Mo_{6.25-7.25}V_3 O_d$$

where d is a number to satisfy the valence of the oxide.

5. The method according to claim 1, wherein the first stream comprises one or more inert diluents, an oxygen containing gas and a gas containing one or more lower alkanes.

6. The method according to claim 1, wherein the second stream comprises one or more unreacted lower alkanes; one or more lower alkenes; oxygen; one or more inert diluents; carbon dioxide; carbon monoxide; acetic acid; and water.

7. The method according to claim 1, wherein the oxidative dehydrogenation reactor comprises a single fixed bed reactor.

8. The method according to claim 1, wherein the oxidative dehydrogenation reactor comprises a single fluidized bed reactor and/or a moving bed reactor.

9. The method according to claim 1, wherein the oxidative dehydrogenation reactor comprises a swing bed reactor arrangement.

10. The method according to claim 1, wherein the group 11 metal is selected from the group of copper, silver, gold and combinations thereof.

11. The method according to claim 1, wherein the group 11 metal is silver.

12. The method according to claim 1, wherein the catalyst in the second reactor comprises at least one member selected from the group consisting of $AgCeO_2/SiO_2$, $AgZrO_2/SiO_2$, $CuCeO_2/SiO_2$ and $CuZrO_2/SiO_2$.

13. The method according to claim 1, wherein an acetic acid scrubber is placed between the oxidative dehydrogenation reactor and the second reactor.

14. The method according to claim 1, wherein the temperature in the second reactor is from 40 to 100° C.

15. The method according to claim 1, wherein the one or more alkenes olefins are used to make olefin derivatives.

16. The method according to claim 15, wherein the olefin derivatives are selected from polyethylene, polypropylene, ethylene oxide, propylene oxide, polyethylene oxide, polypropylene oxide, thermoplastic elastomers, thermoplastic olefins and blends and combinations thereof.

17. The method according to claim 3, wherein the ethylene and the optional α-olefins produced are used to make polyethylene.

18. The method according to claim 17, wherein the polyethylene is selected from homopolymers of ethylene, copolymers of ethylene and α-olefins, HDPE, MDPE, LDPE, LLDPE, VLDPE and combinations and blends thereof.

19. The method according to claim 16, wherein the polyethylene is produced using one or more processes selected from gas phase polyethylene processes, high pressure polyethylene processes, low pressure polyethylene processes, solution polyethylene processes, slurry polyethylene processes and combinations thereon in parallel and/or series reactor configurations.

* * * * *